US012797519B2

(12) United States Patent
Ramaraju et al.

(10) Patent No.: US 12,797,519 B2
(45) Date of Patent: Nov. 17, 2026

(54) PHOTOCURABLE DEVICES AND ADDITIVE MANUFACTURING METHODS OF MAKING THE SAME

(71) Applicant: Georgia Tech Research Corporation, Atlanta, GA (US)

(72) Inventors: Sriharsha Ramaraju, Atlanta, GA (US); Ryan Akman, Atlanta, GA (US); Scott J. Hollister, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 268 days.

(21) Appl. No.: 18/561,058

(22) PCT Filed: Jun. 8, 2022

(86) PCT No.: PCT/US2022/032681
§ 371 (c)(1),
(2) Date: Nov. 15, 2023

(87) PCT Pub. No.: WO2022/261211
PCT Pub. Date: Dec. 15, 2022

(65) Prior Publication Data
US 2024/0226392 A1 Jul. 11, 2024

Related U.S. Application Data

(60) Provisional application No. 63/208,259, filed on Jun. 8, 2021.

(51) Int. Cl.
*A61L 31/06* (2006.01)
*A61L 31/14* (2006.01)
(Continued)

(52) U.S. Cl.
CPC ............... *A61L 31/06* (2013.01); *A61L 31/14* (2013.01); *A61L 31/146* (2013.01);
(Continued)

(58) Field of Classification Search
None
See application file for complete search history.

(56) References Cited

U.S. PATENT DOCUMENTS

2003/0055198 A1 3/2003 Langer et al.
2011/0091518 A1* 4/2011 Biggs .................. A61K 9/0024 424/426
2014/0031913 A1 1/2014 Mashiach

OTHER PUBLICATIONS

Akman, et al., "Development of Photocrosslinked Poly(glycerol dodecanedioate)—A Biodegradable Shape Memory Polymer for 3D-Printed Tissue Engineering Applications," Apr. 24, 2021 Advanced Engineering Materials vol. 23, Issue 10.*

(Continued)

*Primary Examiner* — Melissa S Mercier
(74) *Attorney, Agent, or Firm* — TROUTMAN PEPPER LOCKE LLP; Ryan A. Schneider; Nicholas H. Doss

(57) ABSTRACT

Disclosed herein are implant materials comprising a shape memory polymer having a first shape and a second shape. The shape memory polymer can comprise a polymer backbone having at least one monomer unit of glycerol and at least one monomer unit of dodecanedioate, a photocurable side chain bonded to the polymer backbone, and a photoinitiator. The shape memory polymer can be in the first shape and takes the second shape in response to a stimulus.

24 Claims, 16 Drawing Sheets

(51) Int. Cl.
*A61L 31/16* (2006.01)
*B33Y 70/00* (2020.01)
*B33Y 80/00* (2015.01)
*C08F 283/02* (2006.01)

(52) U.S. Cl.
CPC ............. *A61L 31/148* (2013.01); *A61L 31/16* (2013.01); *B33Y 70/00* (2014.12); *B33Y 80/00* (2014.12); *C08F 283/02* (2013.01); *A61L 2400/16* (2013.01)

(56) References Cited

OTHER PUBLICATIONS

Akman et al. (Development of Photo crosslinked Poly(glycerol dodecanedioate)—A biodegradable shape memory polymer for 3D-printed tissue engineering applications, Advanced Engineering Materials, vol. 23, Issue 10, Apr. 24, 2021) (Year: 2021).*

International Search Report and Written Opinion from Application No. PCT/US2022/032681 dated Nov. 7, 2022.

Akman, et al., "Supporting Information—Development of Photocrosslinked Poly(glycerol dodecanedioate)—A Biodegradable Shape Memory Polymer for 3D-Printed Tissue Engineering Applications," Apr. 24, 2021 Advanced Engineering Materials vol. 23 Issue 10.

Lee, "Synthesis and Characterization of Biodegradable and Thermoresponsive Poly(1,8-octanediol-glycerol-1, 12-dodecanedioate) and its composites for Tissue Engineering Applications," 2017 PHD Thesis, University Teknologi Malaysia.

* cited by examiner

PHOTOCURABLE DEVICES AND ADDITIVE MANUFACTURING METHODS OF MAKING THE SAME

CROSS-REFERENCE TO RELATED APPLICATIONS

This application claims the benefit of U.S. Provisional Application Ser. No. 63/208,259, filed on 8 Jun. 2021, the entire contents and substance of which are incorporated herein by reference in their entirety as if fully set forth below.

FIELD OF THE DISCLOSURE

The present disclosure relates generally to photocurable shape memory polymer devices and methods. Particularly, embodiments of the present disclosure relate to photocurable devices made from bioresorbable implant materials comprising shape memory polymers and additive manufacturing methods of making the same.

BACKGROUND

In tissue engineering, a gap remains in the development of biomaterials for treating soft tissue pathologies that can be deployed via minimally invasive surgical (MIS) techniques and match the target soft tissue's mechanical properties. Despite this gap in the field, MIS procedures are increasing in frequency across multiple fields of medicine due to lower operational costs, shorter length of hospitalization, less adverse events, and in turn lower costs. One major challenge in the treatment of soft tissue pathologies, stemming from acute injury, age related wear, and disease, is the production of biomaterials that exhibit mechanical properties similar to complex tissue mechanical properties. Soft tissues display nonlinear elastic and viscoelastic mechanical properties, requiring similar behavior from potential therapeutic biomaterials to allow for appropriate tissue repair within and around the pathology. These materials should also be biodegradable and bioresorbable in order to allow for tissue infiltration onto and within the implanted device, replacing the pathology with healthy tissue and removing the need for a permanent implant.

Shape memory polymers (SMPs) are a versatile family of materials developed for numerous applications including heat shrinkable tubing, smart textiles, and actuation for soft robotics. SMPs can be leveraged to treat soft tissue pathologies via MIS procedures as materials exhibiting shape memory behavior can fit in a delivery device, and ultimately upon implantation and exposure to body temperature ($T_{trans}$~37° C.), expand to fit the tissue defect. Finally, novel biomaterials developed to solve the challenge of soft tissue treatment via MIS procedures can leverage the rapidly advancing technology of 3D printing to be able to manufacture patient specific devices.

There are a wide range of materials that have been employed to treat soft tissue pathologies, however most of these materials do not exhibit optimal mechanical profiles, biodegradation, and/or shape memory behavior to either treat soft tissue pathologies or be used via MIS treatment methods. Thermoplastic polymers have been used to treat soft tissue pathologies. However, these thermoplastic polymers can yield unfavorable mechanical profiles for some in vivo applications. For example, many of these thermoplastic polymers display linear elastic behavior with Young's moduli in the hundreds of MPa to GPa range, which is far larger than the mechanical properties exhibited by soft tissues. When developing devices to treat soft tissue pathologies, these mechanical properties are crucial as large differences at the interface between device and soft tissue, such as those seen with implanted metallic devices, can lead to tissue erosion or device embolization.

On the other end of the mechanics spectrum, hydrogels exhibit nonlinear elastic and viscoelastic behavior, but are often too compliant to support soft tissue mechanical forces. Furthermore, the use of hydrogels in the clinic is limited by implant migration and rapid resorption, which can necessitate repeat procedures. Unlike thermoplastic polymers and hydrogels, elastomers resist plastic deformation while maintaining elastic behavior under large strains and are able to withstand long-term large cyclic strain. Development of synthetic polymers with nonlinear elastic behavior and adjustable physicochemical properties can yield elastomers more closely suited to the behavior of soft tissue. While these elastomers exhibit promising mechanical profiles for treating soft tissue pathologies, many formulations are not biodegradable, and if they are, their degradation byproducts are not naturally occurring in the human body, which suggests an increased potential for an inflammatory response after implantation.

What is needed, therefore, are bioresorbable, photocurable implant devices and methods of making the same. Embodiments of the present disclosure address this need as well as other needs that will become apparent upon reading the description below in conjunction with the drawings.

BRIEF SUMMARY OF THE DISCLOSURE

The present disclosure relates generally to photocurable devices and methods. Particularly, embodiments of the present disclosure relate to photocurable devices made from bioresorbable implant materials comprising shape memory polymers and additive manufacturing methods of making the same.

An exemplary embodiment of the present disclosure can provide an implant material comprising: a shape memory polymer having a first shape and a second shape, the shape memory polymer comprising: a polymer backbone having at least one monomer unit of glycerol and at least one monomer unit of dodecanedioate; a photocurable side chain bonded to the polymer backbone; and a photoinitiator, wherein the shape memory polymer is in the first shape and takes the second shape in response to a stimulus.

In any of the embodiments disclosed herein, the stimulus can be heat.

In any of the embodiments disclosed herein, the shape memory polymer can be programmed in the first shape by a stimulus comprising visible light, ultraviolet light, infrared light, or a combination thereof.

In any of the embodiments disclosed herein, the photocurable side chain can comprise one or more of: acrylate, acrylamide, methacrylate, methacrylamide, glycidyl methacrylate, hydroxyethyl methacrylate, allyl-clycidyl ether, thiol, norbornene, cinnamate, alkyne, or tyramine.

In any of the embodiments disclosed herein, the photoinitator can comprise one or more of: 2,2-Dimethoxy-2-phenylacetophenone (DMPA), Phenylbis(2,4,6-trimethylbenzoyl)phosphine oxide (BAPO), monoacylphosphine oxide (MAPO), 2,2'-azobis[2-methyl-N-(2-hydroxyethyl) promionamide] (VA-086), and riboflavin.

In any of the embodiments disclosed herein, the shape memory polymer can have a melt transition temperature from approximately 25° C. to approximately 45° C.

In any of the embodiments disclosed herein, the shape memory polymer can be an elastomer above the melt transition temperature and a thermoplastic below the melt transition temperature.

In any of the embodiments disclosed herein, the shape memory polymer can comprise pores ranging from about 0.05 mm to about 10 mm.

In any of the embodiments disclosed herein, the second shape can be a compressed shape for minimally invasive delivery.

In any of the embodiments disclosed herein, the shape memory polymer further comprises a functionalized surface.

In any of the embodiments disclosed herein, the functionalized surface can comprise a plurality of suture holes 3D printed into the functionalized surface.

In any of the embodiments disclosed herein, the functionalized surface can comprise at least one functional group bonded to the shape memory polymer functionalized surface.

In any of the embodiments disclosed herein, at least one functional group can comprise a bioactive agent.

In any of the embodiments disclosed herein, the molar ratio of the at least one monomer unit of glycerol to the at least one monomer unit of dodecanedioate can be from approximately 10:1 to approximately 1:10.

In any of the embodiments disclosed herein, the implant material can have a biodegradation time when implanted in vivo from approximately 4 months to approximately 24 months.

Another embodiment of the present disclosure can provide a method of making an implant, the method comprising forming the implant material of any of the embodiments disclosed herein into one or more of an implant, a patterned mesh, or a molded medical device.

In any of the embodiments disclosed herein, the implant can be in the form of a sheet, a membrane, a mesh, a sponge, a patch, a molded medical device, or a combination thereof.

Another embodiment of the present disclosure can provide a method of making an implant material, the method comprising: forming a shape memory polymer resin comprising at least one monomer unit of glycerol and at least one monomer unit of dodecanedioate; acrylating the shape memory resin; and adding a photoinitiator to the shape memory resin.

In any of the embodiments disclosed herein, the method can further comprise: printing the shape memory polymer resin by additive manufacturing; and exposing the shape polymer resin to visible, UV, or infrared light to form the implant material; wherein the implant material is in a first shape and takes a second shape in response to a stimulus.

In any of the embodiments disclosed herein, the material can be printed with organic or inorganic constituents of tissue extracellular matrices comprising one or more of: hydroxyapatite, calcium phosphate, carbonated apatite, and decellularized and lyophilized soft tissues.

In any of the embodiments disclosed herein, the implant can be post-thermally cured to form ester crosslinks and photosensitive molecular crosslinks In any of the embodiments disclosed herein, the post-thermal curing can be varied to control a number of crosslinks.

In any of the embodiments disclosed herein, the stimulus can be heat.

In any of the embodiments disclosed herein, the implant material can have a melt transition temperature from approximately 25° C. to approximately 45° C.

In any of the embodiments disclosed herein, the implant material can be an elastomer in the first shape and a thermoplastic in the second shape.

In any of the embodiments disclosed herein, the implant material can further comprise a functionalized surface.

In any of the embodiments disclosed herein, the functionalized surface can comprise a plurality of suture 3D printed into the functionalized surface.

In any of the embodiments disclosed herein, the functionalized surface can comprise at least one functional group bonded to the shape memory polymer.

In any of the embodiments disclosed herein, the at least one functional group can comprise a bioactive agent.

In any of the embodiments disclosed herein, the molar ratio of the at least one monomer unit of glycerol to the at least one monomer unit of dodecanedioate can be from approximately 10:1 to approximately 1:10.

In any of the embodiments disclosed herein, the implant material can have a biodegradation time when implanted in vivo from approximately 4 months to approximately 24 months.

Another embodiment of the present disclosure can provide the implant material made according to the method of any of the embodiments disclosed herein.

These and other aspects of the present disclosure are described in the Detailed Description below and the accompanying figures. Other aspects and features of embodiments of the present disclosure will become apparent to those of ordinary skill in the art upon reviewing the following description of specific, exemplary embodiments of the present invention in concert with the figures. While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments of the invention discussed herein. In similar fashion, while exemplary embodiments may be discussed below as device, system, or method embodiments, it is to be understood that such exemplary embodiments can be implemented in various devices, systems, and methods of the present disclosure.

BRIEF DESCRIPTION OF THE DRAWINGS

The accompanying drawings, which are incorporated in and constitute a part of this specification, illustrate multiple embodiments of the presently disclosed subject matter and serve to explain the principles of the presently disclosed subject matter. The drawings are not intended to limit the scope of the presently disclosed subject matter in any manner.

DETAILED DESCRIPTION

Figure 1:
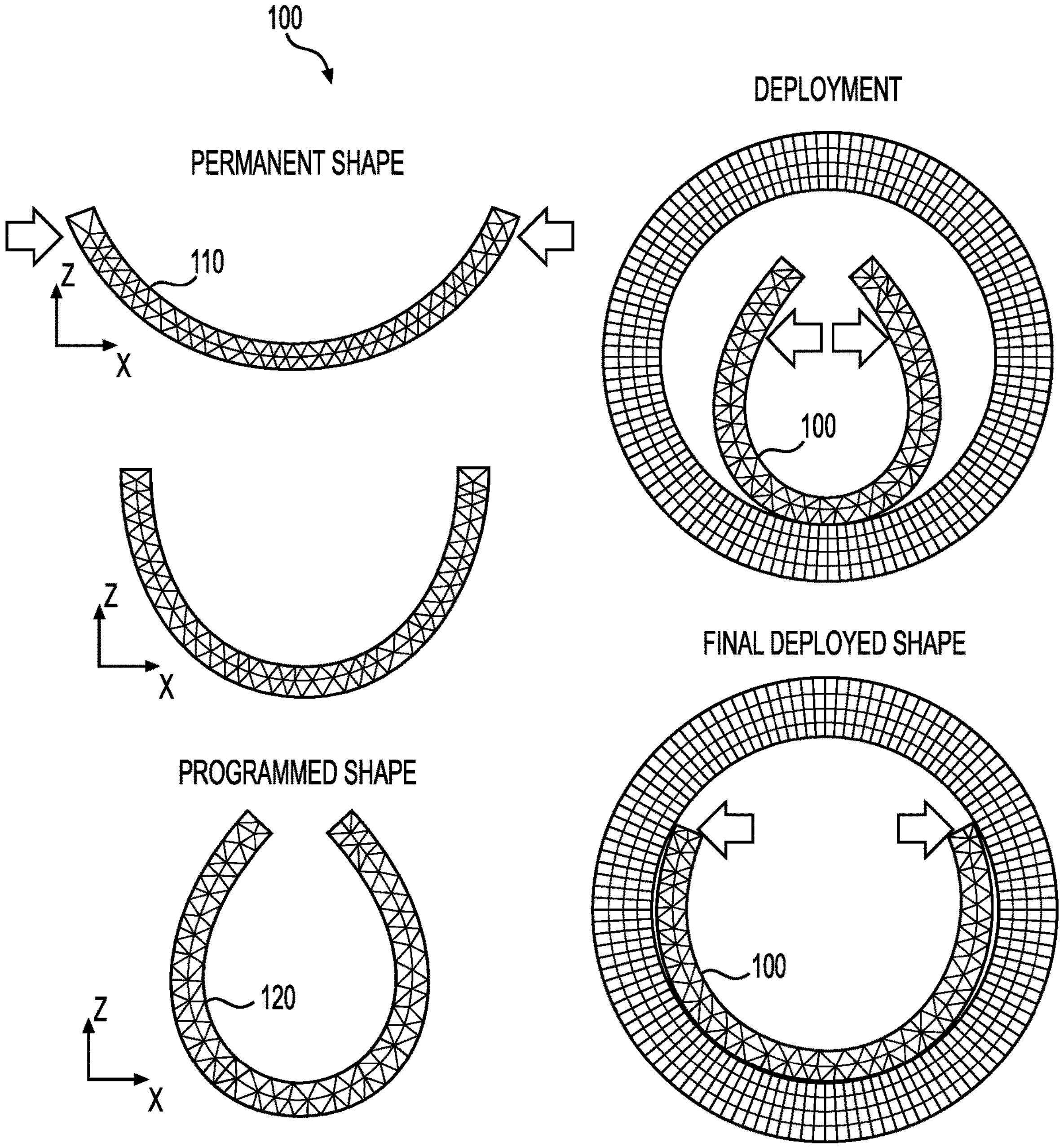
FIG. 1 illustrates an implant material having a first shape and a second shape in accordance with the present disclosure.

Biodegradable elastomers are increasingly sought as a means to treat soft tissue pathology. Like hydrogels, they can be used as cell-seeded vessels or as means of controlled drug release. Additionally, these elastomers can exhibit mechanical properties more closely aligned with native soft tissue such that they are capable of withstanding dynamic environments that might destroy hydrogels. While versatile, some of these elastomers can have harsh curing conditions, such as high temperatures and vacuum, accompanied by long curing reactions which limit their modification. Conversely, photocuring such elastomers can allow for the incorporation of cells or temperature-sensitive molecules directly into the curing polymer.

Photocuring, which can remove the need for molds, allows for in vivo crosslinking or manufacture of complex anatomical structures. Poly(glycerol sebacate) (PGS), one such elastomer for treating soft tissue pathology, initially can use thermal curing, but the addition of acrylate groups to the polymer can allow for photopolymerization. Once photocurable, acrylated PGS (APGS) was used to 3D print complex anatomical structures. Without wishing to be bound by any particular scientific theory, these data suggest an application for APGS in treating soft tissue pathology requiring traditional invasive surgeries. However, APGS can be difficult to use with minimally invasive transcatheter procedures. Instead, a shape memory material that can fit in a catheter at room temperature, but return to a preprogrammed shape at body temperature, can be used. The biodegradable elastomer Poly(glycerol-dodecanoate) (PGD) has the potential to be used in this manner due to its glass transition temperature ($T_g$) of 37° C. Currently, PGD can only be thermally cured, so the present disclosure provides for materials and methods that acrylate PGD (APGD) to develop a photocurable shape memory polymer.

Although certain embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. Other embodiments of the disclosure are capable of being practiced or carried out in various ways. Also, in describing the embodiments, specific terminology will be resorted to for the sake of clarity. It is intended that each term contemplates its broadest meaning as understood by those skilled in the art and includes all technical equivalents which operate in a similar manner to accomplish a similar purpose.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or tricyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-6 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "cycloaliphatic," as used herein, refers to saturated or partially unsaturated cyclic aliphatic monocyclic, bicyclic, or polycyclic ring systems, as described herein, having from 3 to 14 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic," may also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a 'carbocyclic group is tricyclic. In some embodiments, a carbocyclic group is polycyclic. In some embodiments, "cycloaliphatic" (or "carbocycle" or "cycloalkyl") refers to a monocyclic C3-C6 hydrocarbon, or a C8-C10 bicyclic hydrocarbon that is completely saturated or that contains one or more units of unsaturation, but which is not aromatic, that has a single point of attachment to the rest of the molecule, or a C9-C16 tricyclic hydrocarbon that is completely saturated or that contains one or more units of unsaturation, but which is not aromatic, that has a single point of attachment to the rest of the molecule.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has 1-20 carbon atoms in its backbone (e.g., C1-C20 for straight chain, C2-C20 for branched chain), and alternatively, 1-10 carbon atoms, or 1 to 6 carbon atoms. In some embodiments, a cycloalkyl ring has from 3-10 carbon atoms in their ring structure where such rings are monocyclic or bicyclic, and alternatively 5, 6 or 7 carbons in the ring structure. In some embodiments, an alkyl group may be a lower alkyl group, wherein a lower alkyl group comprises 1-4 carbon atoms (e.g., C1-C4 for straight chain lower alkyls).

As used herein, the term "alkenyl" refers to an alkyl group, as defined herein, having one or more double bonds.

As used herein, the term "alkynyl" refers to an alkyl group, as defined herein, having one or more triple bonds.

As used herein, the term "azide" is given its ordinary meaning in the art and may include an alkyl group, as defined herein, having one or more azide functional groups.

The term "heteroalkyl" is given its ordinary meaning in the art and refers to alkyl groups as described herein in which one or more carbon atoms is replaced with a heteroatom (e.g., oxygen, nitrogen, sulfur, and the like). Examples of heteroalkyl groups include, but are not limited to, alkoxy, poly(ethylene glycol), alkyl-substituted amino, tetrahydrofuranyl, piperidinyl, morpholinyl, etc.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, binaphthyl, anthracyi and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone of as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-," as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic, tricyclic, tetracyclic, and/or otherwise polycyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic, tricyclic, tetracyclic, and/or otherwise polycyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation but is not intended to include aryl or heteroaryl moieties, as herein defined.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring.

The term "unsaturated," as used herein, means that a moiety has one or more units of unsaturation.

The term "halogen" means F, Cl, Br, or I; the term "halide" refers to a halogen radical or substituent, namely —F, —Cl, —Br, or —I.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

The term "spiro compound" refers to a chemical compound that presents a twisted structure of two or more rings, in which at least 2 rings are linked together by one common atom, e.g., a carbon atom. When the common atom is located in the center of the compound, the compound is referred to as a "spirocentric compound." The common atom that connects the two or more rings is referred to as the "spiroatom." When such common atom is a carbon atom, it is referred to as the "spiro-carbon."

Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a 11C- or 13C- or 14C-enriched carbon are within the scope of this invention.

Reference will now be made in detail to exemplary embodiments of the disclosed technology, examples of which are illustrated in the accompanying drawings and disclosed herein. Wherever convenient, the same references numbers will be used throughout the drawings to refer to the same or like parts.

FIG. 1 illustrates an implant material 100 having a first shape 110 and a second shape 120. The implant material 100 can comprise a shape memory polymer, and the shape memory polymer can confer properties of the first shape 110 and the second shape 120 to the implant material 100. The shape memory polymer can comprise at least one monomer unit of glycerol and at least one monomer unit of dodecanedioate. Additional other monomer units can be present in the shape memory polymer as desired. Additives can also be added to the shape memory polymer, such as porogens, surfactants, binders, emulsifiers, and the like.

The shape memory polymer can also comprise a photocurable side chain. For example, the shape memory resin can be modified to have a photocurable side chain. The photocurable side chain can comprise, for instance, acrylate, methacrylate, thiolene, norbornene, cinnamate, and the like. The shape memory polymer can also comprise a photoinitiator. The photoinitator can cause the shape memory resin to respond to a stimulus, such as visible light, ultraviolet light, infrared light, or a combination thereof. For example, the photoinitiator can be 2,2-Dimethoxy-2-phenylacetophenone (DMPA), Phenylbis(2,4,6-trimethylbenzoyl)phosphine oxide (BAPO), monoacylphosphine oxide (MAPO), 2,2'-azobis[2-methyl-N-(2-hydroxyethyl) promionamide] (VA-086), riboflavin, and the like.

The ratio of the glycerol to the dodecandeioate can be altered as desired to confer certain properties to the implant material 100. For example, the molar ratio of the at least one monomer unit of glycerol to the at least one monomer unit of dodecanedioate can be from approximately 10:1 to approximately 1:10 (e.g., from 9:1 to 1:10, from 8:1 to 1:10, from 7:1 to 1:10, from 6:1 to 1:10, from 5:1 to 1:10, from 4:1 to 1:10, from 3:1 to 1:10, from 2:1 to 1:10, from 1:1 to 1:10, from 10:1 to 1:9, from 10:1 to 1:8, from 10:1 to 1:7, from 10:1 to 1:6, from 10:1 to 1:5, from 10:1 to 1:4, from 10:1 to 1:3, from 10:1 to 1:2, from 10:1 to 1:1, or from 5:1 to 1:5).

The shape memory polymer can also have a functionalized surface. The functionalized surface can comprise a plurality of suture holes laser cut, or 3D printed into the functionalized surface. The suture holes, or other surface modulations, can be implemented in the implant device 100 to alter the mechanical properties of the implant device 100 as desired. The functionalized surface can comprise, for example, suture holes, grooves, wells, ribs, raised portions, other patterns, and the like. The patterns in the functionalized surface can be patterned using subtractive manufacturing. The functionalized surface can also comprise at least one functional group bonded to the shape memory polymer. The functionalized surface can be conjugated to improve the biocompatibility of the implant material 100. For example, the at least one functional group can be a bioactive agent. The functionalized surface can also be altered to include a plurality of living and/or nonliving cells.

The shape memory polymer can take the first shape 110 at a first environmental temperature and the second shape 120 at a second environmental temperature. The shape memory polymer can have a melt transition temperature from approximately 25° C. to approximately 45° C. (e.g., from 26° C. to 44° C., from 27° C. to 43° C., from 28° C. to 42° C., from 29° C. to 41° C., from 30° C. to 40° C., from 31° C. to 39° C., from 32° C. to 38° C., from 33° C. to 37° C. from 34° C. to 36° C., from 30° C. to 39° C., from 31° C. to 38° C., from 31° C. to 37° C., from 31° C. to 36° C., or from 31° C. to 35° C.). The melt transition temperature can be greater than or equal to the first environmental temperature and less than the second environmental temperature. Alternatively, or in addition, the shape memory polymer can be an elastomer above the melt transition temperature and a thermoplastic in the below the melt transition temperature.

The first shape 110 can be considered a "permanent" or recovered shape. In other words, the implant material 100 can be configured to return to the first shape when no stimulus is present. The first shape 110 can be a curved or tubular shape. The second shape 120 can be a "programmed" or stimulated shape. In other words, the implant material 100 can be configured to take the second shape 120 in response to a stimulus, such as temperature, light, pH, and the like. For example, the implant material 100 can take the second shape in response to a temperature stimulus of the second environmental temperature being greater than the first environmental temperature. The second shape 120 can be a tubular shape comprising a cut along a longitudinal axis of the implant material 100. The second shape 120 can be manipulated or minimized/compressed for minimally invasive delivery.

By way of another example, the permanent shape can be a curve and the programmed shape can be tubular. When subjected to stimulus of a cold temperature, the implant material 100 can take the programmed shape and behave as a thermoplastic below the melt transition temperature. When implanted into a warm environment, the implant material 100 can recover to the permanent shape when implanted and behave as an elastomer above the melt transition temperature.

Furthermore, the implant material can have a biodegradation time when implanted in vivo from approximately 4 months to approximately 24 months (e.g., from 5 months to 23 months, from 6 months to 22 months, from 7 months to 21 months, from 8 months to 21 months, from 9 months to 20 months, from 10 months to 20 months, from 10 months to 15 months, from 5 months to 15 months, from 4 months to 10 months, or from 12 months to 24 months).

Figure 2:
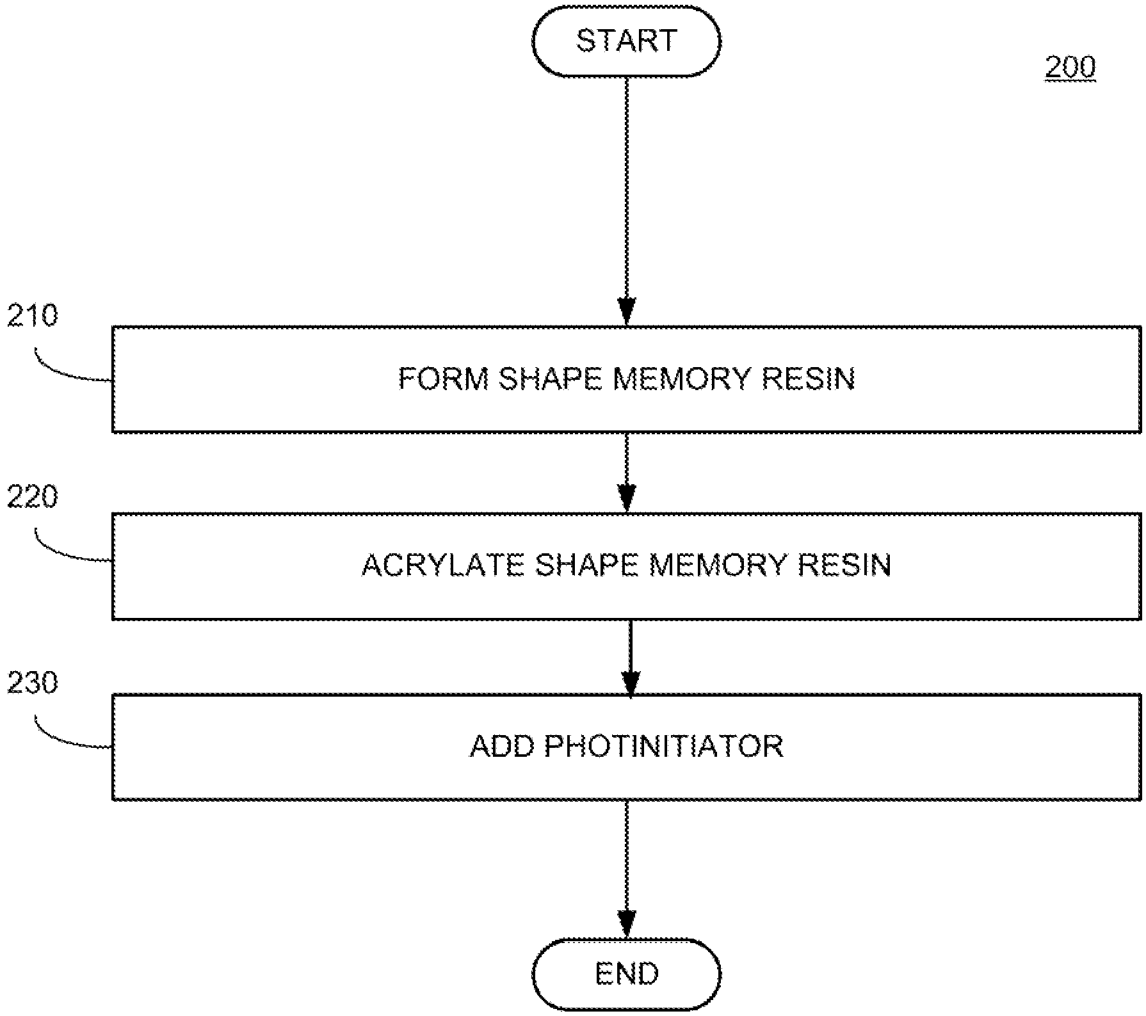
FIG. 2 illustrates a flowchart of a method of making an implant material in accordance with the present disclosure.

FIG. 2 is a flowchart of a method 200 of making an implant material 100. As shown in block 210, the shape memory resin can be formed. The shape memory resin can be 3D printed. In some examples, the shape memory resin can be formed by a mold, and the mold can have various patterns to impart surface geometry to the functionalized surface of the implant material 100. The various patterns in the mold can have features having a size of approximately 5 microns or greater. The mold can also be surface treated with a nonfouling release agent, such as parylene. The method 200 can then proceed on to block 220.

In block 220, the shape memory resin can be acrylated. For example, the shape memory resin can be modified to have a photocurable side chain. The photocurable side chain can comprise, for instance, acrylate, methacrylate, thiolene, norbornene, cinnamate, and the like. The method 200 can then proceed on to block 230.

In block 230, a photoinitator can be added to the shape memory resin. The photoinitiator can cause the shape memory resin to respond to a stimulus, such as visible light, ultraviolet light, infrared light, or a combination thereof. For example, the photoinitiator can be 2,2-Dimethoxy-2-phenylacetophenone (DMPA), Phenylbis(2,4,6-trimethylbenzoyl) phosphine oxide (BAPO), monoacylphosphine oxide (MAPO), 2,2'-azobis[2-methyl-N-(2-hydroxyethyl) promionamide] (VA-086), riboflavin, and the like.

The shape memory elastomer can be fully cured to form the implant material 100. The implant material 100 can be fully cured at a variety of temperatures, temporal durations, and pressures as desired to yield desirable properties in the implant material 100, such as crosslink density and toughness. The shape memory elastomer can also be fully cured in a permanent shape such that the implant material 100 takes on a permanent shape. For example, the shape memory elastomer can be fully cured on a roller such that the implant material 100 is a tubular shape. The method 200 can terminate after block 230. However, the method 200 can also proceed on to other method steps not shown.

Figure 3:
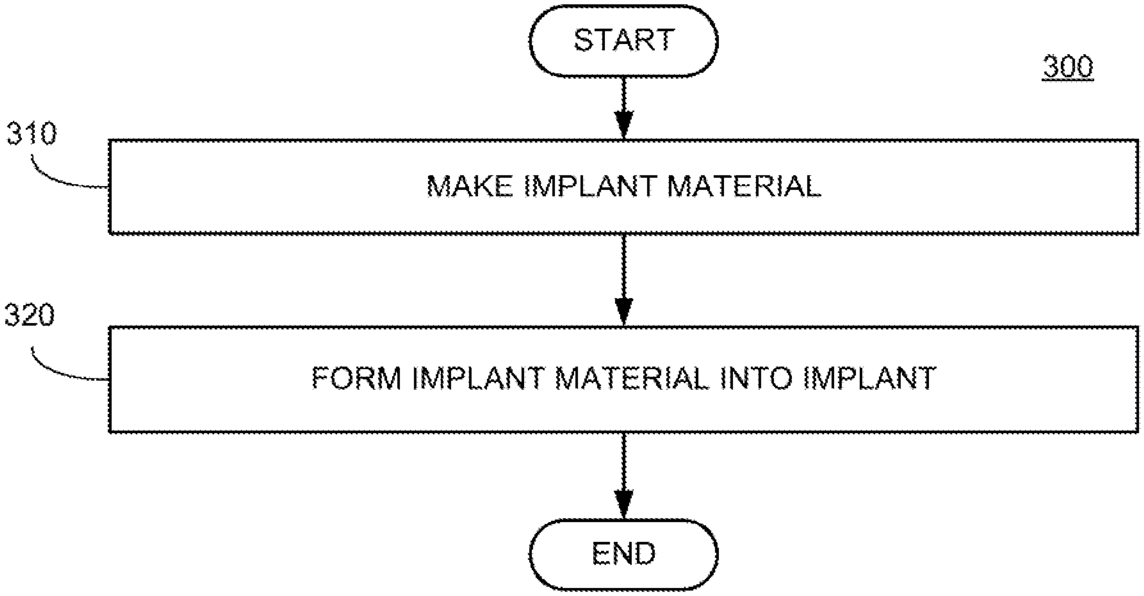
FIG. 3 illustrates a flowchart of another method of making an implant material in accordance with the present disclosure.

FIG. 3 is a flowchart of another method 300 of making an implant material 100. In block 310, the implant material 100 can be made through any of the methodologies as described herein. In block 320, the implant material 100 can be formed into an implant. The implant can be in the form of a sheet, a membrane, a mesh, a sponge, a patch, a molded medical device, or combinations thereof. The implant can also be functionalized as described herein such that the implant has a functionalized surface. For example, the implant can comprise organic or inorganic constituents of tissue extracellular matrices comprising hydroxyapatite, calcium phosphate, carbonated apatite, decellularized and lyophilized soft tissues, and the like.

Certain embodiments and implementations of the disclosed technology are described above with reference to block and flow diagrams of systems and methods and/or computer program products according to example embodiments or implementations of the disclosed technology. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, may be repeated, or may not necessarily need to be performed at all, according to some embodiments or implementations of the disclosed technology.

EXAMPLES

The following examples are provided by way of illustration but not by way of limitation.

Example 1

Poly(glycerol dodecanedioate) (PGD) can exhibit a clinically relevant $T_m$ of 37±1.1° C. At room temperature PGD can act as a stiff isotropic-elastic material, and at body temperature it can behave in a compliant non-linear elastic manner. PGD can behave with tangent elastic moduli ranging from 5 to 5 MPa and 70 to 80% elastic deformation, making it a promising material for use in MIS procedures aimed at the treatment of soft tissue pathologies. In addition to its favorable mechanical and shape memory properties, PGD can be synthesized through a polycondensation reaction of the nontoxic monomers glycerol and dodecanedioic acid, indicating that PGD can yield biocompatible degradation byproducts.

PGD exhibits non-linear elastic mechanical profiles, biocompatible monomers, and shape memory behavior, but there are still significant logistical challenges to advancing PGD from the benchtop to the clinic. Specifically, PGD is a thermoset polymer where crosslinks are induced via thermal curing conditions. Thermoset polymers exhibit critical disadvantages compared to photoset polymers with regards to clinical translation of the intended material. Thermoset polymers require harsh curing conditions, such as high temperatures and vacuum, to establish crosslinked networks. These conditions limit potential therapeutics or small molecules that could be added to the thermoset polymer for tissue specific applications. In addition, some clinical applications may require, or be improved by, the use of in vivo curing. Photosetting polymers can be delivered and exposed to UV light in a clinical setting, allowing for in vivo curing, while thermoset polymers typically cannot be utilized in this manner due to safety concerns.

Most importantly for PGD, thermal curing significantly limits the ability to manufacture patient specific devices using the thermoset polymer because it takes multiple days to crosslink these polymer networks. Devices can be thermally cured in molds, but molds are often unable to produce the highly complex structures required for clinical translation of patient specific devices, and when they can they are neither economically feasible nor rapidly reproduced. Conversely, the chemistry of photosetting polymers typically can induce rapid crosslinking which allows these materials to be 3D printed on commercial machines that either have built-in UV sources or which can be readily modified to include them.

Disclosed herein is the use of acrylation chemistry to produce photocurable PGD and the effects of acrylation percentage (Acr %) on subsequent novel APGD materials. Acrylation was chosen because it is a thoroughly studied and well-understood chemistry that has been used with other thermosets to induce photocurable behavior. The development of photocurable APGD can reduce the time to cure from days to seconds, and this rapid cure behavior can be leveraged to produce novel 3D printable APGD resins.

Prior to 3D printing APGD, it is critical to determine how Acr % affects APGD material properties to determine which formulation is best matched for repairing specific soft tissues. Disclosed herein are relationships illustrating how Acr % affects APGD polymer network crosslink density, APGD $T_m$, shape fixity and recovery ratios, in vitro degradation, surface chemistry, tangent Young's moduli, and strain at break. After examining these APGD materials, a select APGD resin can be chosen for 3D printing based on its ideal translational behavior with $T_m$ between 20-37° C., excellent shape fixity and recovery ratios, and promising biocompatibility. Such an APGD resin can be successfully 3D printed on an extrusion printer and 3D printed samples can be shown to maintain shape memory behavior while exhibiting non-linear elastic and large deformation behavior. The ability to 3D print such APGD resins can be important to the field of tissue engineering as only a small number of elastomeric SMPs have been 3D printed, with only two of these previously developed 3D printed SMPs being biodegradable.

Significant differences in complex viscosity can be measured between PGD pre-polymers synthesized over 24 and 48 h respectively prior to melting at 48° C. Samples made using 24 and 48 h PGD pre-polymer from herein will be referred to as low molecular weight (LMW) and high molecular weight (HMW) APGD respectively, based on viscosity measurements. Acrylation can be confirmed by 1H qNMR with acrylated samples showing peaks at 5.9, 6.2 and 6.4 ppm. Peak integration can be used to calculate Acr % which can reveal a good fit to theoretical values. Photocured APGD samples can show clear shape memory behavior where the sample can be deformed into a programmed shape and upon heating returned to its permanent shape. Below APGD network $T_m$, the material can present as a stiff thermoplastic material exhibiting linear elastic behavior with opaque white coloration. Upon heating above $T_m$, the polymer can transition to an elastomer with translucent morphology.

Figure 4A:
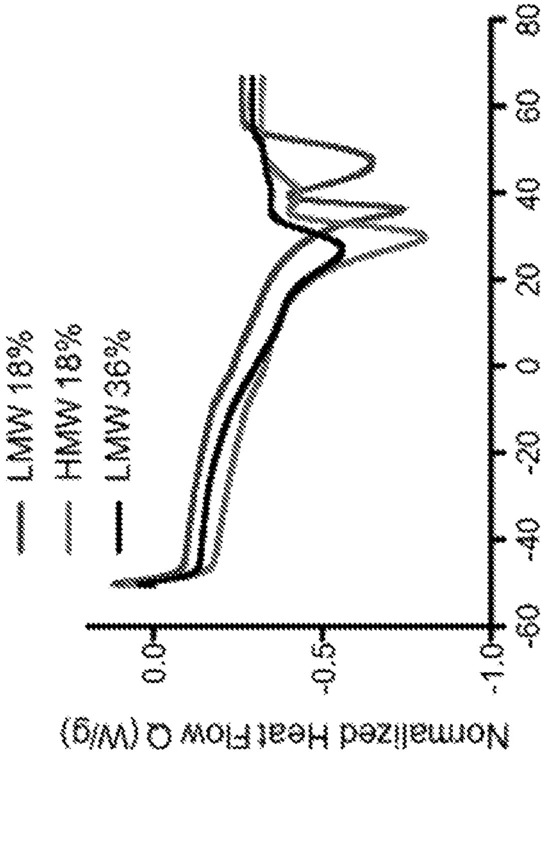
FIGS. 4A and 4B illustrate material properties of an implant material as a function of temperature, in accordance with the present disclosure.

APGD samples can be tested via differential scanning calorimetry (DSC) to determine changes in $T_m$ as a function of Acr % and MW (FIGS. 4A and 4B); the transition temperature ($T_{trans}$) of APGD can be a melt transition, as evidenced by the melting peaks observed within the temperature range in which the APGD transitions from plastic to rubbery behavior. This behavior suggests APGD can be a chemically crosslinked semi-crystalline rubber, as defined by the SMP Mather classification, placing APGD in the same family of polymers as PGD and polydiolcitrate networks. FIG. 4A shows that as Acr % increases, $T_m$ decreases. Thermally cured PGD (120° C., 68 h) can have a $T_m$ of 37±1.1° C., similar to the $T_m$ of LMW 18% APGD at 36.2±0.3° C., whereas LMW 36% APGD measured a $T_m$ much closer to room temperature. Increased PGD MW can also reduce APGD $T_m$ as shown by the HMW 18% APGD $T_m$ of 28.7±0.9° C., which is lower than the $T_m$ measured for LMW 18% APGD. Both the increase in Acr % and PGD MW yielded transition curves with a single peak; LMW 18% measured a transition curve with two peaks, whereas both LMW 36% and HMW 18% measured transition curves with a single peak. Relative crystallinity of the APGD polymer networks can be inferred from enthalpy of fusion ($\Delta H_{fusion}$). Increasing Acr % of LMW PGD from 18% to 36% can reduce relative crystallinity, as shown by $\Delta H_{fusion}$s of 41.8±2.1 J/g and 21.2±0.8 J/g. Intermediate LMW APGD groups can show a linear trend of reduced crystallinity with respects to increased Acr % as well. Conversely, increased PGD MW can increase relative crystallinity of the samples as shown by HMW 18% APGD's $\Delta H_{fusion}$ of 47.1±3.8 J/g.

Initially, the DSC thermogram of LMW 18% APGD can exhibit a biphasic transition curve, indicative of two thermally distinct crystalline regions within the polymer network (FIG. 4A). Increased Acr % can lead to a thermogram yielding one transition peak as seen with the LMW 36% APGD sample. This reduced heterogeneity within the APGD network can be indicative of increasing crosslink density in conjunction with increasing Acr %. The increased acrylation can increase crosslink density thereby reducing mobility of longer polymer chains, restricting formation of crystalline lamellae, and reducing the overall entropy within the network. In turn, crystallinity of the polymer network can be reduced with increasing crosslink density as shown by the lower enthalpy of fusion ($\Delta H_{fusion}$) measured for LMW 36% as compared to LMW 18% APGD networks.

PGD MW can also play a role in the heterogeneity of the APGD polymer networks, as demonstrated by the melt transition curve measured for HMW 18% APGD. Unlike the LMW 36% APGD, this transition from biphasic to single transition curve peak is not due to a substantial increase in polymer network crosslink density. Instead, without wishing to be bound by any particular scientific theory, it can be the increased MW of the HMW sample that is driving this change. Increased polymer molecular weight can be associated with increased crystallinity, as longer chain lengths provide more energetically favorable environments for the formation of crystalline lamellar structures, which can be demonstrated here by the larger $\Delta H_{fusion}$ of HMW versus LMW polymer networks at 18% acrylation. Here, the increase in network crystallinity can serve to reduce overall material heterogeneity, which consolidated the two thermal regions seen in the LMW 18% samples leaving a single transition curve measured through DSC.

Figure 4B:
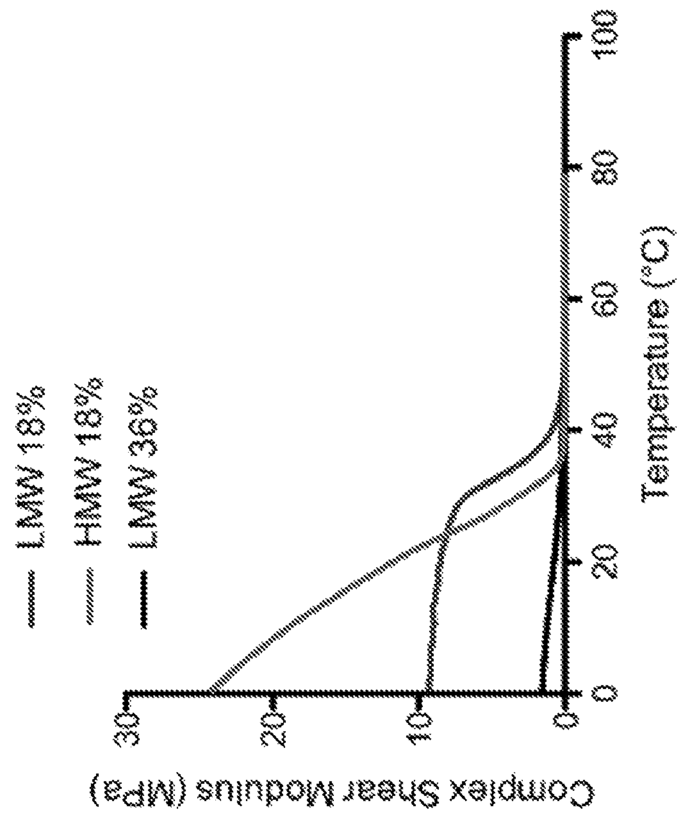

Dynamic mechanical thermal analysis on a rheometer using a temperature sweep corroborated DSC data, showing $T_m$ can decrease as a function of Acry % (FIG. 4B, Table 1). The drop in $T_m$ can be more subtle than that seen from the DSC analysis. From 18-27% LMW APGD, $T_m$ can be effectively the same but the measured complex shear modulus of 22.5 and 27% LMW APGD can be lower than that of LMW 18% APGD. Compared to all other APGD polymers, the LMW 36% APGD can show a pronounced drop in both $T_m$, which can be measured at 17.3±7.7° C., and complex shear modulus below its measured $T_m$. Rheometry analysis can also show that increased PGD MW can reduce APGD $T_m$. HMW 18% APGD can exhibit a $T_m$ of 33.4±0.1° C. compared to the $T_m$ of LMW 18% APGD measured at 39.4±0.5° C. HMW 18% APGD shear modulus at $T_m$ can be lower than all other APGD percentages except for the LMW 36% sample.

In addition, the rheometry data can show that increased Acry % and PGD MW can lead to reduced complex shear moduli at T>37° C. Without wishing to be bound by any particular scientific theory, this means that both increased Acr % and PGD MW can reduce the stiffness of resultant APGD materials in shear near or at body temperature. DSC analysis can provide insight into the underlying molecular architecture of tested samples, allowing calculation of sample material properties including crosslink density, crystallinity, and $T_m$ (for an unloaded sample). However, DSC cannot measure how thermal transitions affect material mechanical properties, which is why rheometry can be used to calculate $T_m$ from APGD specimens while samples were subjected to shear loading. This testing provides a more accurate representation of the in vivo environment the materials will experience moving forward.

TABLE 1

$T_m$ measured via DSC and rheometry with enthalpy of fusion.

| | $T_m$ - DSC (° C.) | $\Delta H_{fusion}$ (J/g) | $T_m$ - Rheometry (° C.) |
|---|---|---|---|
| LMW18% | 36.2 ± 0.3 | 41.8 ± 2.1 | 39.4 ± 0.5 |
| HMW 18% | 28.7 ± 0.9 | 47.1 ± 3.8 | 33.4 ± 0.1 |
| LMW 36% | 26.7 ± 0.3 | 21.2 ± 0.8 | 17.3 ± 7.7 |

Contact angle measurements can be taken between water and APGD thin film samples. LMW 18% APGD can exhibit significantly lower contact angle measurements compared to all other samples (p<0.01). Conversely the LMW 22.5% APGD can yield significantly higher contact angle measurements compared to all other LMW APGD samples (p<0.05). Above 22.5%, Acr % did not cause significant differences in the contact angles measured between LMW APGD samples. Increased PGD MW can significantly increase the contact angle measurements of HMW 18% compared to LMW 18% APGD (p<0.0001). The increased Acr % of HMW 27% APGD did not yield significant differences in contact angle measurements compared to HMW 18% APGD. By raising Acry % in the acrylated polymer coatings, surface contact angle can increase, and water absorption can decrease. The ramifications of these differences in APGD surface chemistry are further explored in relation to their effects on in vitro degradation and cell attachment.

Figure 5:
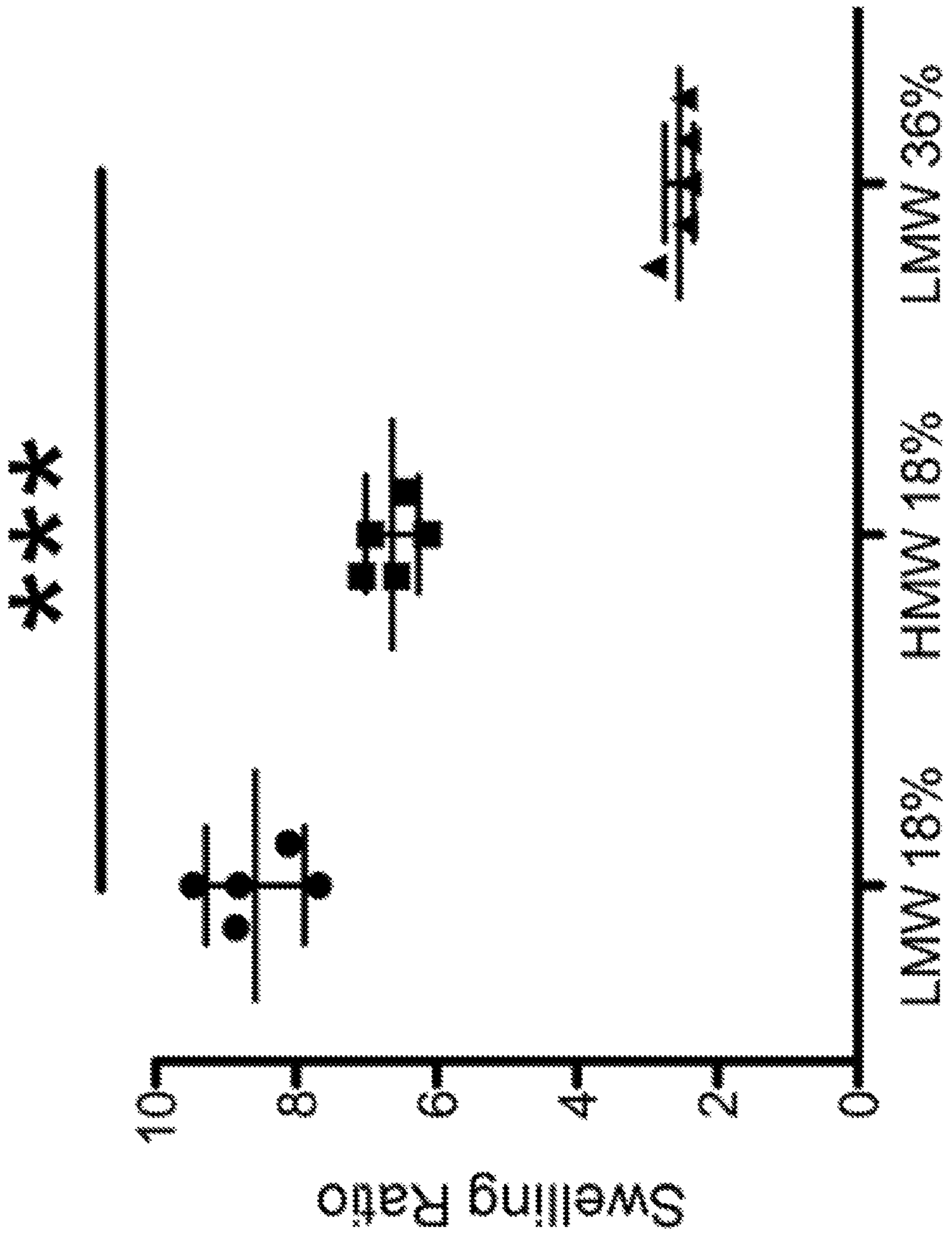
FIG. 5 illustrates a plot of solvent swelling ratios for examples of an implant material in accordance with the present disclosure.

APGD samples can be swelled in tetrahydrofuran (THF) and, as Acr % increased, the samples' swelling ratios can show significant decreases across all groups (FIG. 5, p<0.0001). Increased PGD MW can also reduce sample swelling, as HMW 18% APGD measured a significantly reduced swelling ratio compared to the LMW 18% APGD (p<0.0001). These swelling data can be used to calculate both gel content and crosslink density for the tested APGD polymer networks. Without wishing to be bound by any particular scientific theory, reductions in swelling due to increased Acr % can correlate to increases in both gel content and crosslink density for LMW APGD samples; gel content increased from 36.9±1.5 to 69.1±1.1%, while crosslink density increased from 13.9±3.7 to 379.1±61.9 mol/m$^3$ for LMW 18 and 36% APGD samples respectively. Due to the reduced swelling recorded for HMW 18% samples, their calculated gel content and crosslink density values, 46.4±4.5% and 30.3±5.1 mol/m$^3$ respectively, can be larger than those recorded for LMW 18% APGD as well.

Crosslink density calculated from swelling ratios can suggest that increased Acr % can increase crosslink density. HMW 18% APGD can display a swelling ratio between that of 18% and 36% LMW APGD, suggesting that the increased crystallinity of the high MW samples can reduce the polymer's swelling ratio, but to a lesser extent compared to the effect of increased crosslink density.

Figure 6A:
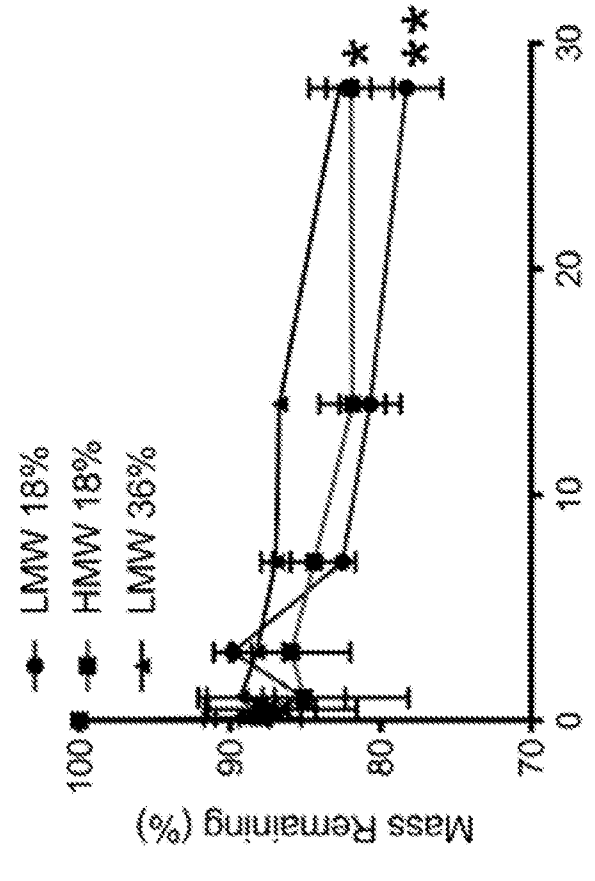
FIGS. 6A and 6B illustrate plots of degradation and volume loss for examples of an implant material in accordance with the present disclosure.

The in vitro degradation profiles of all APGD samples, in PBS (0.1 mM NaOH), can show significant mass loss as a function of time (p<0.0001), with 18 and 36% LMW APGD showing the largest and smallest mass losses respectively (FIG. 6A). Across all timepoints, the LMW 18% APGD can show significantly higher levels of degradation compared to all other APGD percentages (p<0.01). HMW 18% APGD samples can show significantly higher degradation compared to the 22.5 and 36% LMW APGD samples (FIG. 6A, p<0.05). While differences in MW can cause significant differences in swelling ratios of LMW and HMW 18% APGD samples, there were no significant differences in degradation between these two groups over the 28-day measurement period. In addition to mass loss, all APGD samples can demonstrate significant loss in volume with respect to time (p<0.01) as a result of the in vitro degradation process (FIG. 5).

The differences in APGD network crosslink density appear to be key drivers in the in vitro degradation of these APGD materials. Specifically, the LMW and HMW 18% APGD samples can measure significantly increased degradation rates compared to the LMW 36% APGD group over the measured 28 days (FIG. 6A). Without wishing to be bound by any particular scientific theory, the relationship between increasing crosslink density and reduced degradation rate has been noted for other acrylated polymers in addition to APGD. Crystallinity of the APGD networks can appear to be less influential on the degradation kinetics of the APGD samples, as the HMW and LMW 18% APGD groups measured no significant difference between their degradation profiles.

Figure 6B:
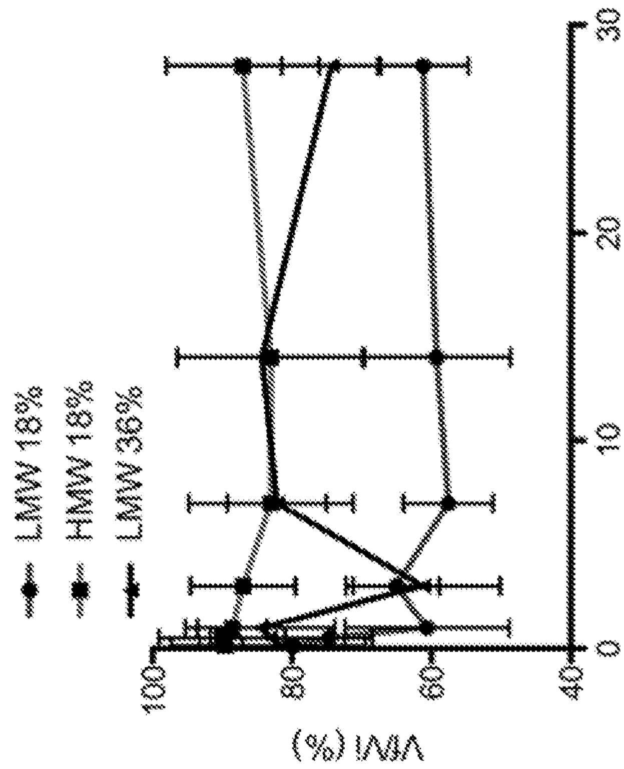

Interestingly, the surface chemistry of the APGD samples can also have little impact on the degradation of the APGD networks. The measured contact angles of most of the APGD networks can be relatively similar with the notable exception of the LMW 18% APGD, which can measure a significantly reduced contact angle compared to all the other APGD samples. This suggests that both increased Acr % and PGD MW can reduce the hydrophilicity of APGD polymer networks. It may appear unusual that LMW and HMW 18% APGD degrade at the same rate when the former polymer is more hydrophilic than the latter. However, without wishing to be bound by any particular scientific theory, APGD appears to be following a surface mediated degradation profile where hydrolysis of the polymer backbone dominates the action of diffusion in the degradation of the polymer network. Polymers yielding surface mediated degradation can measure linear degradation profiles, as the degradation is directly proportional to the loss of mass from the surface of the samples as hydrolysis rapidly takes place. APGD samples can clearly exhibit linear in vitro degradation profile, suggesting APGD undergoes surface mediated degradation (FIG. 6A). Surface mediated degradation can also lead to reduced sample dimensions, whereas bulk degradation mass loss is not correlated to significant dimensional reduction. All APGD samples tested can measure significant losses in volume over the course of the 28-day in vitro degradation assay, reinforcing the role of surface mediated APGD degradation via in vitro testing (FIG. 6B). APGD's surface mediated degradation is not surprising, as thermally cured PGD can also demonstrate surface mediated degradation via in vitro and in vivo assays. A material's hydrophilicity can play a larger role in the case of bulk degradation, as hydrophilicity can increase the diffusion of solvent into and out of a polymer network leading to faster removal of degradation byproducts.

Figure 7:
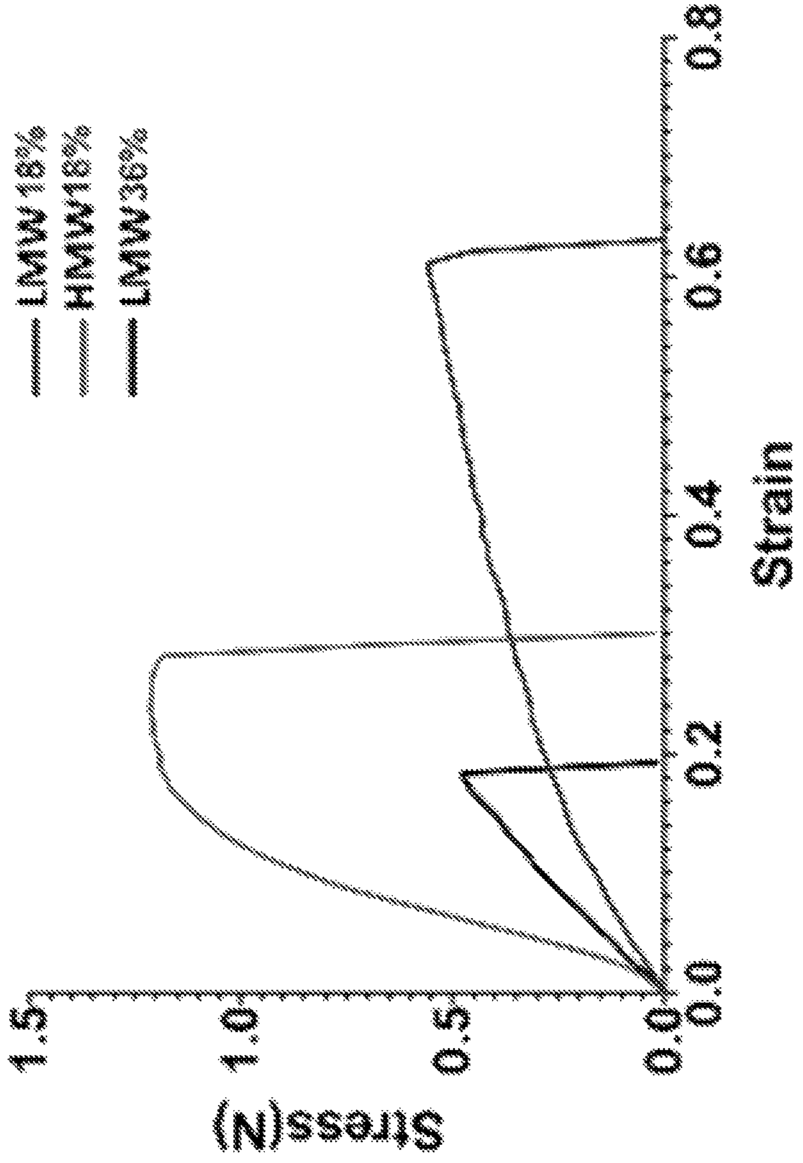
FIG. 7 illustrates a plot of stress-strain curves for examples of an implant material in accordance with the present disclosure.
Figure 8A:
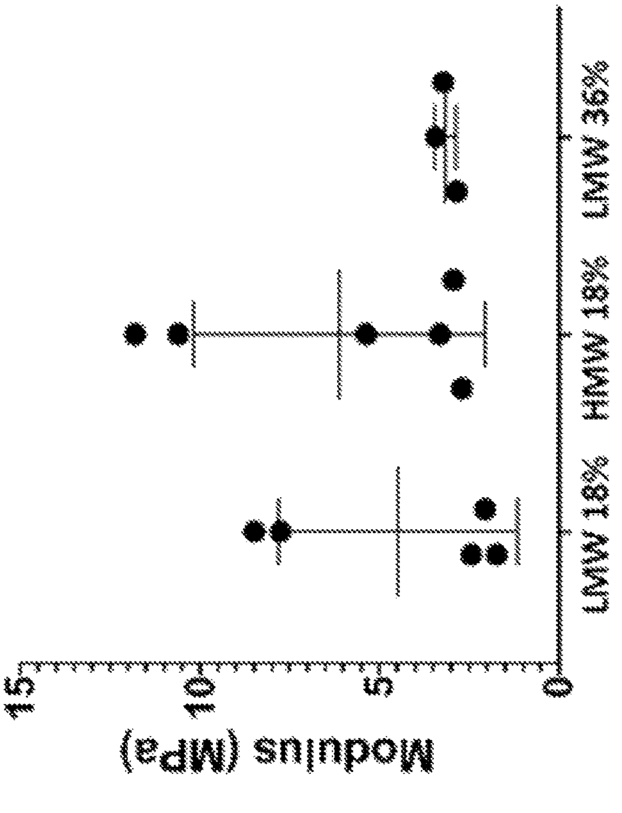
FIGS. 8A and 8B illustrate plots of the Young's Modulus and the strain at break, respectively, for examples of an implant material in accordance with the present disclosure.
Figure 8B:
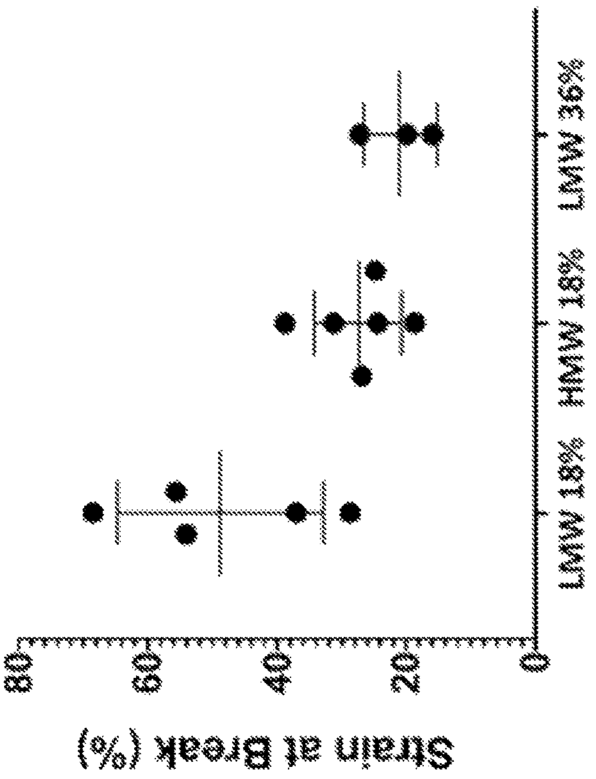

APGD dogbone samples can be tested in uniaxial tension until failure in a 37° C. water bath (FIG. 7). Tangent Young's modulus calculated at 5% strain can show no differences as a function of either change in Acr % or PGD MW (FIG. 8A). Strain at break can be noted for all samples and while the means of the groups decreased as a function of Acr % and increased MW, no groups achieved significance in their differences (FIG. 8B). Given that increasing Acr % increased the crosslink density of these materials, APGD samples with higher Acr % can exhibit more stiff behavior, yielding larger Young's modulus and lower strain at break. However, across all groups tested there were no significant differences between either Young's modulus or strain at break. This can be due to the tested materials all having different $T_m$s, where the larger the difference between the $T_m$ and the test temperature (37° C.), the less stiff the material can behave. This relationship between $T_{trans}$ and polymer mechanics is similar to glassy chemically crosslinked methacrylate SMPs, where a small decrease in $T_g$ can lead to a decrease in rubbery moduli at the same test temperatures. For this reason, it is plausible that there are no significant differences seen in this assay as increasing APGD Acr % can lead to decreasing $T_m$, offsetting any increasing stiffness due to the increased APGD crosslink density. It is possible that if these APGD materials are tested at their respective $T_m$s then they can exhibit significant differences in Young's modulus and strain at break.

Shape fixity ratio measurements can be performed to determine how well samples maintained their programmed shapes at room temperature (Table 2). Increased Acr % can lead to significant decreases in the shape fixity ratio ($p<0.0001$). Specifically, LMW 36% APGD can measure a lower shape fixity ratio compared to all other groups, while LMW 27% APGD can yield a significantly lower shape fixity ratio compared to 18 and 22.5% APGD samples (Table 2, $p<0.0001$). HMW 18% APGD can show a large shape fixity ratio, with measurements comparable to LMW 18% and higher than LMW 36% ($p<0.0001$).

Following shape fixity ratio measurements, samples can be immersed in water at 37° C., and both shape recovery ratios and recovery rate can be measured. Both shape recovery ratio and recovery rate in water at 37° C. can increase with higher Acr %. Recovery rates for all APGD groups can increase as a function of increased Acr % ($p<0.05$). Increased PGD MW can also lead to an increased shape recovery ratio and recovery rate measurement compared to the LMW APGD materials. Specifically, HMW 18% APGD can demonstrate a higher shape recovery ratio and recovery rates compared to LMW 18% APGD ($p<0.05$, $p<0.01$). HMW 18% APGD can yield the best overall shape recovery properties of all APGD materials tested.

Changes in Acr % and PGD MW can lead to significant changes in the shape fixity ratios, shape recovery ratios, and recovery rates of APGD samples. Both LMW and HMW 18% APGD can show a significantly increased shape fixity ratio compared to LMW 36% APGD (Table 2). The shape fixity ratio can decrease as a function of Acr % considering the full set of acrylation percentages (Table 2). In these APGD networks, crosslinks can act as netpoints to establish the permanent shape of the network while the crystalline regions in between the crosslinks can act as molecular switches which establish the temporary shape of the network. Increasing Acr %, and a subsequent increase in crosslink density, can reduce APGD network crystallinity as the increased number of crosslinks disrupts the formation of crystalline lamellae. Due to the reduced number of crystalline regions, APGD networks with increasing Acr % can yield samples with reduced shape fixity ratios as they lack the molecular switches to establish temporary shapes with high fidelity. In addition, the LMW 36% APGD can measure a $T_m$ at or below room temperature, via DSC and rheometry, and, given the shape fixity tests were conducted at room temperature, this can explain in part the large decrease in shape fixity ratios for these samples as they were partially recovering to their permanent shape.

TABLE 2

Shape fixity and shape recovery ratio measured at room temperature for examples of an implant material in accordance with the present disclosure.

| | LMW 18% | HMW 18% | LMW 36% |
|---|---|---|---|
| Shape Fixity Ratio (%) | 97.7 ± 3.7*** | 97.1 ± 4.3*** | 39.9 ± 9.0 |
| Shape Recovery Ratio (%) | 78.4 ± 0.8 | 90.2 ± 4.7* | 88.4 ± 6.9 |
| Recovery Rate (rad/min) | 4.9 ± 0.6 | 8.6 ± 0.5** | 19.7 ± 1.6*** |

Considering the shape recovery test was performed at 37° C., and increasing Acr % lowers APGD $T_m$, it is not surprising that the shape recovery ratio can increase, and recovery rate can decrease in relation to increasing Acr %. Interestingly, the HMW 18% APGD group can measure a significantly higher shape recovery ratio and shape recovery rate compared to its LMW counterpart. Both groups can have a similar number of crosslinks due to measuring a similar Acr %, therefore these increases in shape recovery and shape recovery rate can be directly related to the increase in PGD MW.

In work evaluating the shape memory behavior of polydiolcitrate networks, the use of longer chain hydrophobic diols (12 versus 8 carbons) can induce shape memory properties in the resultant polymer due to thermodynamically favored intermolecular packing. While these citrate polymers are different from the described PGD, both polymers can experience similar intermolecular hydrophobic interactions, which can explain the improved shape memory features seen in the HMW versus LMW 18% APGD. In addition, this can explain why PGD exhibits shape memory features as compared to PGS, due to the fact that PGD can have two additional carbons in its polymer backbone raising the backbone hydrophobicity to a point where these shape memory features are thermodynamically favored.

The soybean oil epoxidized acrylate has a $T_{trans}$ below room temperature, challenging its ability to be used in clinical translation, while the PTMC-PLA copolymer can require significant quantities of organic solvent to be mixed into the resin to be printed, a roadblock to its use in biological applications. The 3D printable APGD resin disclosed herein can have a $T_{trans}$ between 20-37° C. and does not require solvent to be 3D printed.

After producing 3D printed dogbones, the final test of 3D printing can be to determine whether the APGD resin can be used to produce structures that could be used in tissue engineering applications. Extrusion 3D printing can show the capability of printing complex 3D scaffold structures with APGD that can be readily adapted for in vitro or in vivo biological assays. In addition, the ability to print the APGD resin using a range of line widths can allow for greater flexibility when printing structures at different scales and resolutions.

PGD is a bionspired shape memory polymer designed specifically with tough elastomeric properties, to emulate soft tissue, while also taking advantage of polyester chemistries designed to mimic natural compounds the human body could resorb post degradation. Compared to other polyesters, like PCL and PLLA, these bioinspired materials have only been recently synthesized and characterized, demonstrating results that can affect the direction of biomaterial design in the field of soft tissue engineering. Through the synthesis of APGD, disclosed herein are photocurable bioinspired polymers with shape memory behavior. Amongst the broader field of SMPs, polymers can be acrylated to induce shape memory properties.

The present disclosure can illustrate that increasing APGD Acr % can increase polymer network crosslink density, leading to reduced $T_m$ and complex shear modulus measured at $T>T_m$. Increased APGD Acr % can also be shown to reduce APGD in vitro degradation and can yield substantial changes in sample shape memory behavior, with subsequent decreases and increases in shape fixity and recovery respectively. Cell behavior can also be affected by APGD acrylation. Cytotoxocity assays can show increasing Acr % can yield improved cell survival up to 36% APGD. Cell proliferation assays can measure improved cell proliferation at two weeks on APGD of higher Acr %, which can be reinforced by improved cell spreading at 24 h on APGD materials above 18% acrylation in the conducted cell attachment assays. These differences between the indirect cytotoxicity assay and direct cell proliferation and attachment assays can be connected in part to the effect of higher Acr % reducing the surface hydrophilicity of APGD polymer networks. These tests can also be performed with two distinct LMW and HMW PGD batches. HMW APGD can be shown to yield a more crystalline polymer network, which can cause a reduction in APGD $T_m$, improved shape fixity, recovery and recovery rates, and improved cell attachment and proliferation. Given the generally improved material properties of the HMW 18% APGD, such a material can be used as a prototype resin for the 3D printing of APGD which can be shown to be possible through the printing of dogbone and scaffold structures. 3D printed structures can also be shown to retain their shape memory behavior.

APGD resin can be further characterized for 3D printing applications. With improved understanding of the behavior of the disclosed resins, complex anatomical structures can be printed via extrusion 3D printing. The disclosed APGD can transition from the benchtop to the clinic via the production of prototype devices to treat soft tissue pathologies including, but not limited to, ruptured ear drums, cleft palate defects, and esophageal atresia. The mechanics of the disclosed samples, with tangent moduli in the 0-10 MPa range, can be positioned to match these different types of soft tissue. By exhibiting stiffness well below the GPa range, APGD materials can have a reduced risk of damaging surrounding tissue after implantation. Exhibiting shape fixity ratios and shape recovery ratios close to 100% can allow for APGD devices to be set into a programmed shape suitable for storage in a delivery device and ultimately, upon delivery and exposure to body temperature, recover to the permanent shape to appropriately address the target pathology. In vivo tests can be performed to understand how APGD will degrade in animal models, but preliminary in vitro assays can show approximately 15-20% degradation over a 1-month time period suggesting APGD is biodegradable and is a promising material for use in applications where a permanent implant is not desired.

PGD pre-polymer can be synthesized via condensation reaction between equimolar parts glycerol and dodecanedioic acid. This mixture can be stirred at 120° C. under nitrogen for 24 h and then placed under vacuum (−28 in. Hg) for either 24 or 48 h. PGD can be acrylated by dissolving the pre-polymer in dichloromethane containing triethylamine, 4-methoxyphenol and 4-dimethylamino pyridine. Acryloyl chloride can be added to solution to approximately 0.18-0.36 mol/mol hydroxyl groups on the PGD pre-polymer. 0.5 wt % 2,2-Dimethoxy-2-phenylacetophenone (DMPA) can be added as photoinitiator to allow for sample curing under 365 nm UV light.

1H qNMR (Varian Mercury Vx 400) samples can be analyzed with 90° pulse-width of 15.5 s and a recycle decay of 25 s. Samples can be dissolved in CDCL3, which can be used as a reference at 7.27 ppm. 1H qNMR data can be used to confirm theoretical Acr % of all APGD networks. Below is a table outlining the synthesis conditions and confirmed Acr % of some non-limiting examples of APGD variants tested in the present disclosure.

TABLE 3

Synthesis conditions and acrylation percentage for examples of an implant material in accordance with the present disclosure.

| | Prepolymer under vacuum | Theoretical Acrylation | Measured Acrylation |
|---|---|---|---|
| LMW 18% | 24 h | 18% | 18.08% |
| LMW 22.5% | 24 h | 22.5% | 22.88% |
| LMW 27% | 24 h | 27% | 26.53% |
| LMW 36% | 24 h | 36% | 37.11% |
| HMW 18% | 48 h | 18% | 18.44% |
| HMW 27% | 48 h | 27% | 28.15% |

The difference in time under vacuum can be used to produce PGD pre-polymer of two different MWs, where 24 and 48 h batches can be labeled low molecular weight (LMW) and high molecular weight (HMW) APGD respectively. The MW of PGD pre-polymer can be unable to be measured directly by GPC, but 48 h PGD pre-polymer can exhibit a higher viscosity than 24 h PGD pre-polymer, which can suggest through the Mark-Houwink equation, that 48 h PGD pre-polymer can have a higher MW compared to 24 h PGD pre-polymer. PGD Pre-polymer viscosity measurements can be conducted using an Anton Paar MCR 302, measuring viscosity over a temperature range of 35 to 65° C. with constant. 1% shear strain and 0.6 rad/s angular frequency.

DSC (TA Instruments DSC 250) samples (4×2 mm, n=3) can be heated from 20 to 90° C. (20° C./min). Samples can be held at 90° C. for 3 min. Samples can be cooled from 90 to −50° C. (10° C./min) and were held at −50° C. for 3 min. Samples can then be heated to 70° C. (10° C./min). Sample $T_m$s can be calculated using the Trios software peak integration (enthalpy) function. Rheometry (Anton Paar MCR 302) samples (8×2 mm, n=3) can be heated from −10 to 80° C. at a constant heating rate, while subjected to constant shear strain. The loss factor (tan 8) and loss modulus can be plotted versus temperature and their intersection can be defined as the reported $T_m$.

Samples (6×2 mm, n=5) can be swollen in 5 mL tetrahydrofuran (THF) at 37° C. and weighed daily. After 3 days of swelling, samples can reach equilibrium swollen mass. Samples can be dried overnight at 90° C. and weighed to determine the mass of the dry sample.

Samples (6×2 mm, n=4) can be submerged in 10 mL of phosphate buffered saline (PBS) with 0.1 mM NaOH at 37° C. Samples can be removed at designated time points and their dimensions (height and diameter) can be measured via electronic caliper. Samples can then be dried overnight at 90° C. Samples can be weighed after drying to determine mass loss.

Samples (5×30×2 mm, n=3) can be cut from cured APGD sheets. Samples can be set in a horizontal orientation (180°) for their permanent shape at the time of curing. Samples can then be heated above $T_{trans}$ at 45° C. and can be set in a programmed "C" shape with 20° between the ends of the samples. Samples can be set in the programmed shape through cooling below sample $T_m$ (T<0° C.) and can be subsequently allowed to return to room temperature overnight. Sample programmed angles can be measured at a stress-free condition and then immersed in a 37° C. water where final recovery angle and time to recover can be recorded. Shape fixity ratio, shape recovery ratio, and recovery rate can be calculated via the following equations:

$$\text{Shape Fixity Ratio} = 100 - \left(\frac{\theta_{programmed} - \theta_{theoretical}}{\theta_{theoretical}}\right) * 100,$$

$$\text{where } \theta_{theoretical} = 20^\circ$$

$$\text{Shape Recovery Ratio} = 100 - \left(\frac{\theta_{recovered} - \theta_{programmed}}{\theta_{permanent} - \theta_{programmed}}\right) * 100,$$

$$\text{where } \theta_{permanent} = 180^\circ$$

$$\text{Recovery Rate} = \frac{\theta_{recovered} - \theta_{programmed}}{\text{time}}$$

APGD samples can be cured directly in untreated well plates. APGD can be washed in complete media for 6 days with media changes every 2 days. NIH3T3 cells can be seeded directly onto the APGD. Cells can be cultured out to 1, 3, 7, 10 and 14 days where they were collected in CellLytic M (Sigma Aldritch) lysis buffer. Complete cell lysis can be ensured through 3 freeze thaw cycles. Cell DNA can be measured following the protocol of a Picogreen Assay Kit (ThermoFisher P11496). Cell number can be estimated assuming 6 pg DNA/mammalian cell and this value can be corroborated via cell counts prior to seeding.

APGD samples can be cured directly in untreated well plates. APGD can be washed in complete media for 6 days with media changes every 2 days. NIH3T3 cells can be seeded directly onto the APGD. Cells can be allowed to attach for 1, 3, 6, 12 and 24 h and can be fixed in 10% NBF. Cells can be stained in Rhodhamine-Pholloidin (Life Technologies) and DAPI. Representative regions of cells can be imaged using a Zeiss LSM 700 confocal microscope at 20× magnification. Cell area can be calculated using ImageJ (v. 2.0.0).

Tensile dogbone specimens can be manufactured in the ASTM D638 Type V format (n=4-5). Specimens can be tested using a Test Resources 574LE2 Planar Biaxial Tester and can be strained under uniaxial tension, at a rate of 10 mm/min, using 2 of the 4 actuators. All tensile tests can be conducted at 37° C. and can be continued until the samples fractured. Force and displacement data can be used to calculate stress and strain respectively. The slope of the stress strain curve can be calculated to measure the tangent Young's Modulus of the samples from 5% strain to break. Strain at break can be defined as the highest strain value prior to fracture of the sample.

HMW 18% APGD can be synthesized with 0.5 wt % DMPA and can be used as a photocurable resin. Samples can be printed using an Inkredible Plus 3D printer (CellInk) with additional UV lights attached to the printer. ASTM D638 Type V dogbone samples can be printed using a 400 μm diameter nozzle via a metallic printhead (Musashi). STL files can be uploaded to the printer's slicing software (Cellink HeartWare 2.4.1, Cellink) and can be sliced with 100% infill. Scaffold structures can be printed using 250, 300, and 400 μm diameter nozzles (Musashi). STL files of an 8×4 mm cylinder can be uploaded to the printer's slicing software (Cellink HeartWare 2.4.1, Cellink) and can be sliced using the default Cellink "Tissue Model" setting to produce scaffold structures with 14.5% infill. Samples can be exposed to 365 nm UV light throughout the 3D printing process to ensure each layer fully cured prior to additional material deposition.

One and Two-way ANOVA with Tukey's post hoc tests can be performed on JMP Pro 14 along with Student's T-Tests, where p values $<0.05$ were considered statistically significant. Sigmoidal curve fits and IC50 calculations can be performed on Graphpad Prism 5.

PGD prepolymer can be synthesized via condensation reaction and cured as described previously. PGD can be acrylated and photocured in a similar manner as described above for PGS. 1H nuclear magnetic resonance (NMR) can be performed using a Varian Mercury Vx 400. Attenuated total reflectance-fourier transform infrared spectroscopy (ATR-FTIR) can be performed using a Shimadzu Prestige 21 Infrared Spectrometer. Differential scanning calorimetry (DSC) can be performed on a TA Instruments DSC 250. Dynamic shear rheometry (DSR) can be performed using an Anton Paar MCR 302.

Example 2

As disclosed herein, APGD acrylation percentage can have an effect on polymer crosslink density, melt transition temperature ($T_m$), in vitro degradation, shape memory behavior, cytotoxicity, cell proliferation, and cell attachment. The present disclosure can investigate how changes in APGD resin chemistry can impact rheological properties of these resins. A range of APGD resins can be characterized via real time measurements of UV curing to determine how the acrylate crosslinker and photoinitiator (PI) concentrations affect time to gel point, viscosity prior to crosslinking, and post-polymerization storage modulus. In addition, two different PIs, 2,2-Dimethoxy-2-phenylacetophenone (DMPA) and Phenylbis(2,4,6-trimethylbenzoyl)phosphine oxide (BAPO), can be used to cure the APGD resins at 365 and 405 nm respectively; the two PIs can be used because the E and DLP printers in this study use 365 and 405 nm UV excitation respectively. Rheology of the resin can be used for evaluating printability using either DLP or E modalities. In E printing, knowing the viscosity of the resin can be important as it will impact the print pressure, printhead temperature, and printhead geometries required to extrude the resin in a controlled and accurate manner. As such, the viscosity of the resin can play a role in the resolution of E printing dependent on individual 3D printers. For DLP printing, gel time data can inform print parameters including exposure time and resin viscosity to eliminate print damage resulting from high viscous forces.

As disclosed herein, the first DLP 3D printed APGD and new aspects of E 3D printed APGD can be reported. Following photorheometry experiments, the remainder of the present disclosure can compare the geometric, material, and mechanical properties of APGD samples printed using both E and DLP 3D printers. Specifically, differences between design and sample geometry/volume, void volume, transition temperature, complex shear modulus, swelling ratio and gel content, nonlinear Neo-Hookean APGD properties, stress and strain at break, and shape memory behavior including shape fixity ($R_f$), shape recovery ($R_r$), and recovery rate ($dR_r/dt$) were characterized. A manufacturing control group, APGD resin set in molds and cured using 365 nm UV light with samples cut out of the cured material via laser cutting (LC), can be used to provide a test group without the layer-by-layer structures imparted by E and DLP printers.

Given the different advantages E and DLP printing offer, determining underlying differences in the resultant prints can be an input for deciding which modality is best for specific applications. As disclosed herein, APGD resin can be used across 2 printing modalities to isolate the effects of the manufacturing modalities themselves. This study demonstrates the effect of different print modalities on resultant sample material properties providing important advances in the field of 3D printable biomaterials for patient specific soft tissue structural repair in minimally invasive procedures.

APGD was synthesized as described above. Briefly, PGD pre-polymer can be synthesized via a condensation reaction between equimolar parts glycerol (Sigma-Aldrich, St. Louis, MO) and dodecanedioic acid (Sigma-Aldrich, St. Louis, MO). This mixture can be stirred at 120° C. under nitrogen for 24 h and then placed under vacuum (−28 in. Hg) for 48 h. PGD can be acrylated by dissolving the pre-polymer in dichloromethane containing triethylamine (Fisher Scientific, Hampton, NH), 4-methoxyphenol (Alfa Aesar, Haverhill, MA) and 4-dimethylamino pyridine (Sigma-Aldrich, St. Louis, MO). Acryloyl chloride (Sigma-Aldrich, St. Louis, MO) can be added to solution to approximately 0.09-0.27 mol/mol hydroxyl groups on the PGD pre-polymer. Acrylation percentage can be confirmed via 1H qNMR (Varian Mercury Vx 400), where samples can be analyzed with 90° pulse-width of 15.5 s and a recycle decay of 25 s. 2,2-Dimethoxy-2-phenylacetophenone (DMPA, Sigma-Aldrich, St. Louis, MO) and Phenylbis(2,4,6-trimethylbenzoyl)phosphine oxide (BAPO, Sigma-Aldrich, St. Louis, MO) can be added as photoinitiators to allow for sample curing under 365 or 405 nm UV light respectively; 0.25-1 wt % PI can be used to synthesize these resins. 0.5 vol % Tartrazine (FD&C yellow #5, Sigma-Aldrich, St. Louis, MO) can be added as a photoabsorbent to APGD resin using the BAPO photoinitiator to reduce off target curing during DLP printing.

UV cure assays (n=3) can be performed on an MCR 302 rheometer (Anton Paar) using a UV light guide module (P-PTD 200/GL, Anton Paar) connected to a UV light source (Omnicure S2000). APGD resin can be melted at 50° C. and 100 μm layers can be photopolymerized with exposure to 365 nm or 405 nm UV light (10 mW $cm^{-2}$). Live measurements of the storage and loss moduli can be recorded using a parallel plate geometry (25 mm) under constant shear strain (0.1%) and frequency (10 Hz) at 50° C. Gel time can be recorded as the time at the gel point, or by definition when the sample storage moduli (G') intersected the loss moduli (G"). The storage modulus can be recorded as the average of the last 10 data points of the storage modulus curve, signifying the plateau value of the storage modulus.

Samples (2×8 mm, n=10) can be scanned on a μCT40 (Scanco Medical) system using 16 μm voxel size. Voltage and current can be set to 55 kVp and 145 μA, respectively. Sample and void volume can be assessed using the native μCT40 evaluation software (v6.1, Scanco Medical) using a threshold of 43.

Differential scanning calorimetry (DSC) can be conducted using a DSC 250 (TA Instruments). Samples (4×1 mm, n=3) can be heated from 20 to 90° C. (20° C./min). Samples can be held at 90° C. for 3 min. Samples can be cooled from 90 to −50° C. (10° C./min) and can be held at −50° C. for 3 min. Samples can then be heated to 70° C. (10° C./min). Sample $T_m$ and enthalpy of fusion ($\Delta H_{fusion}$) can be calculated using the Trios software (TA Instruments) peak integration (enthalpy) function. Rheometry can be conducted using a MCR 302 rheometer (Anton Paar). Samples (8×2 mm, n=3) can be heated from −10 to 80° C. at a constant heating rate, while subjected to constant shear strain. The loss factor (tan 8) and loss modulus can be plotted versus temperature and their intersection can be defined as the reported $T_m$.

Samples (6×2 mm, n=10) can be swollen in 5 mL tetrahydrofuran (THF) at 37° C. and weighed daily. After 3 days of swelling, samples can reach equilibrium swollen mass (ms). Samples can be dried overnight at 90° C. and weighed to determine the mass of the dry sample (md). Swelling ratio and gel content can be calculated using the following equations:

$$\text{Swelling Ratio} = ((m_s - m_d)/m_d)$$

$$\text{Gel Content} = \left(\frac{m_d}{m_0}\right) * 100,$$

where $m_0$ is the sample mass prior to solvent swelling.

Rectangular samples (5×30×2 mm, n=10) of APGD can be tested for shape memory behavior as described herein. In brief, APGD samples can be set in a horizontal orientation (180°) for their permanent shape at the time of curing. Samples can be then heated above $T_m$ at 45° C. and can be set in a programmed "C" shape with 20° between the ends of the samples. Samples can be set in the programmed shape through cooling below sample $T_m$ (T<0° C.) and can be subsequently allowed to return to room temperature overnight. Sample programmed angles can be measured at a stress-free condition and then immersed in 37° C. water where final recovery angle and time to recover can be recorded. Shape fixity ($R_f$), shape recovery ($R_r$), and recovery rate ($dR_r/dt$) can be calculated via the following equations:

$$R_f(N) = \frac{\theta_u(N)}{\theta_m}$$

$$R_r(N) = \frac{\theta_m - \theta_p(N)}{\theta_m - \theta_p(N-1)}$$

$$\frac{dR_r}{dt}(N) = \frac{\theta_m - \theta_p(N)}{\Delta t}$$

where N is any given shape memory cycle, $\theta_u(N)$ is the temporary angle created by the mechanical deformation $\theta_m$, $\theta_p(N)$ is the permanent angle the material recovers to after the deformation $\theta_m$, $\theta_m-\theta_p(N)$ is the change in angle over the course of recovery and $\theta_m-\theta_p(N-1)$ is the change in angle over the course of programming.

Tensile dogbone specimens can be manufactured as proportionally half size (X, Y, and Z dimension) ASTM D638 Type V format (31.75×5.5×1 mm, n=8-10). Specimens can be tested using a Test Resources 574LE2 Planar Biaxial Tester under uniaxial tension, at a rate of 10 mm/min. All tensile tests can be conducted at 37° C. and can be continued until the samples fractured. Force and displacement data can be used to calculate stress and strain, respectively. These stress and strain data can be used to fit APGD samples to a Neo-Hookean non-linear elastic model:

$$W(\lambda_1, \lambda_2, \lambda_3) = \frac{C_1}{2}\left(\lambda_1^2 + \lambda_2^2 + \lambda_3^2 - 3\right)$$

W is the strain energy function and $\lambda_1$, $\lambda_2$, $\lambda_3$ are stretch ratios. $C_1$ is a material constant fit to the experimental stress-strain data. FEBio studio (v 1.6.1) can be used to fit C1 for all APGD samples. R2 values can be calculated in MATLAB (v 2021b) to determine the accuracy of the Neo-Hookean model fits. Stress at break can be defined as the calculated stress at the data point prior to sample fracture, while strain at break can be defined as the highest strain value prior to fracture of the sample.

Control samples can be produced using a silicone mold and laser cutter. 4 mL of melted APGD resin (0.5 wt % DMPA) can be pipetted into rectangular silicone molds (2.5×5 cm) where the APGD resin can then be exposed to 365 nm UV light (VioletII, MelodySusie) for 2 min. Samples for each assay can then be laser cut out of the rectangular APGD sheets. E samples can be printed using an Inkredible Plus 3D printer (CellInk) with additional UV lights (VioletII, MelodySusie, 365 nm) attached to the printer. Samples can be printed with APGD resin (0.5 wt % DMPA) using a 250 μm diameter nozzle via a metallic printhead (Musashi). STL files can be uploaded to the printer's slicing software (Cellink HeartWare 2.4.1, Cellink) and can be sliced with 100% infill. Samples can be exposed to 365 nm UV light throughout the 3D printing process to ensure each layer fully cured prior to additional material deposition. Typical print parameters can include printhead temperature of 40° C., pressure of 500 kPa, and print speed of 20 mm $s^{-1}$. DLP samples can be printed using a Lumen X (Cellink) bioprinter. APGD resin can be initially melted at 50° C. and subsequently heated on the Lumen X print bed at 37° C. throughout the print. APGD resin (0.5 wt % BAPO, 0.5 vol % tartrazine) can be used for printing on the Lumen X given the printer's UV source provides 405 nm light. Tartrazine can be used in the resin as a photoabsorbent to reduce off target curing. Samples can be printed with 10 s/layer exposure time and 67% projector power level (35 mW $cm^{-2}$).

One, two, and three-way ANOVA with Tukey's post hoc tests can be performed on Graphpad Prism 9, where p values <0.05 can be considered statistically significant. Given three-way ANOVA can only run with 1 variable at more than 2 levels, data from either the 9% acrylation groups or the 0.25% PI groups could be assessed using this test. The 0.25% PI group can be chosen for assessment as 9% resins can be deemed unprintable due to lack of curing and long gel times.

Figure 9:
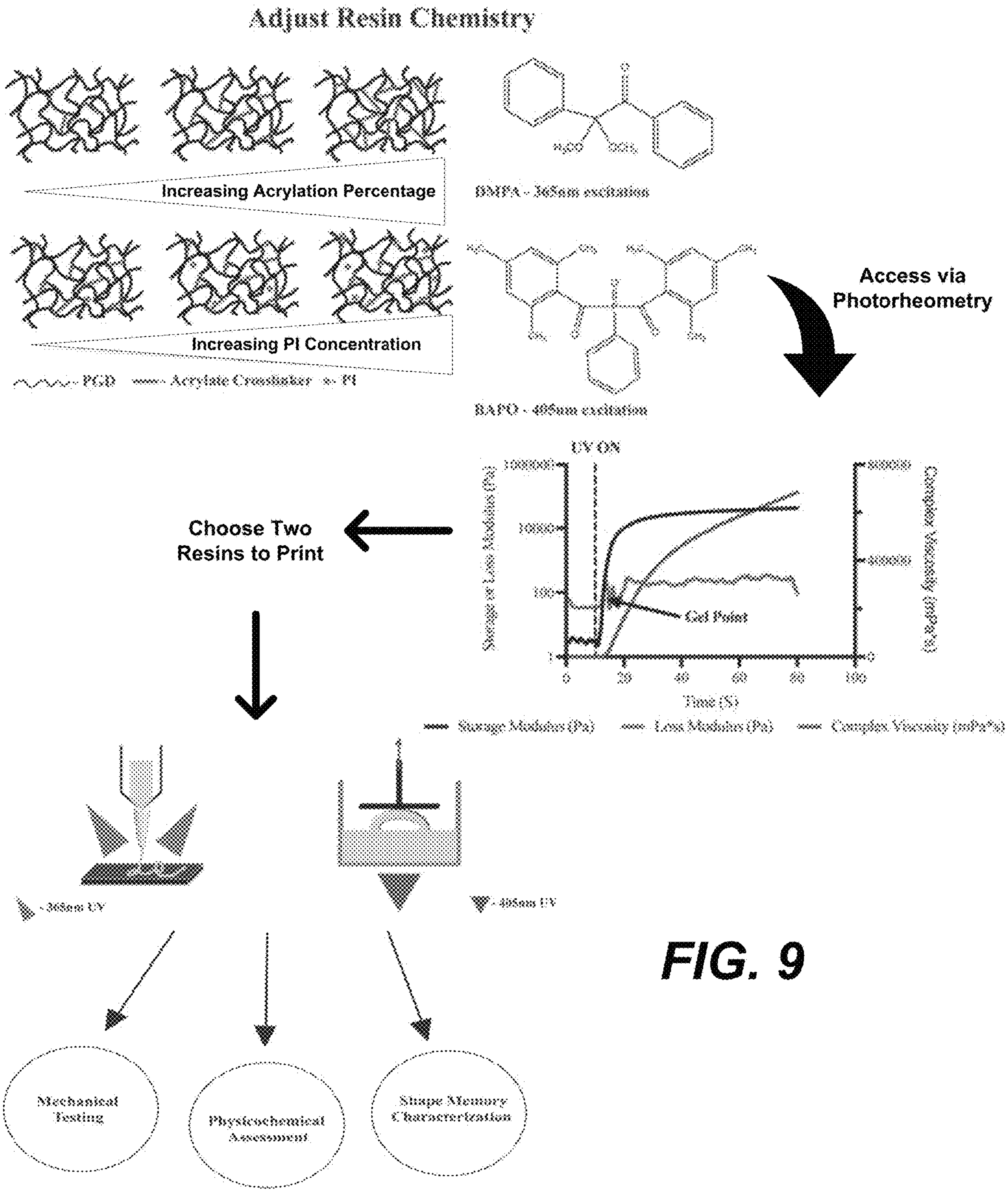
FIG. 9 illustrates an example diagram of a method of making an implant material in accordance with the present disclosure.

FIG. 9 provides a basic overview of the workflow of the present disclosure. Initially, a range of APGD resins can be synthesized using varying acrylate percentage (9, 18, 27%), PI concentration (0.25, 0.5, 1%), and PI (DMPA or BAPO). Photorheometry can be used to assess material properties of the APGD resins including complex viscosity prior to crosslinking, gel time, and storage modulus after crosslinking. These material properties can then be used to help determine appropriate resins to 3D print samples for the remainder of the characterization performed throughout the study. Specifically, a complex viscosity and gel time of 2 Pa*s and 10 s, respectively, can be used as upper limits for viability of printable resins, with preference for resins using lower amounts of acrylate and PI.

Figure 10B:
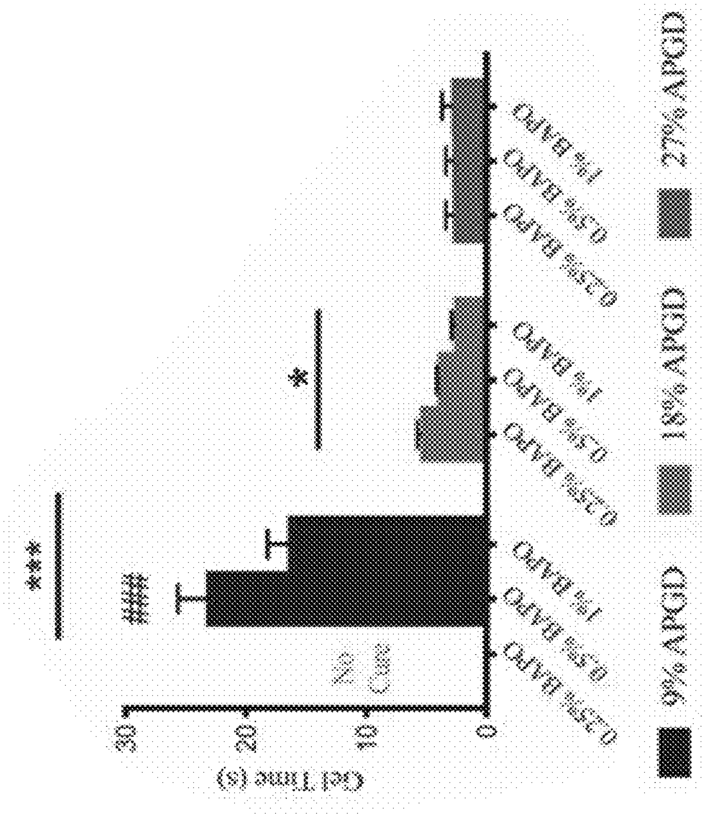
FIGS. 10A and 10B illustrate charts of gel time for examples of an implant material in accordance with the present disclosure.
Figure 10A:
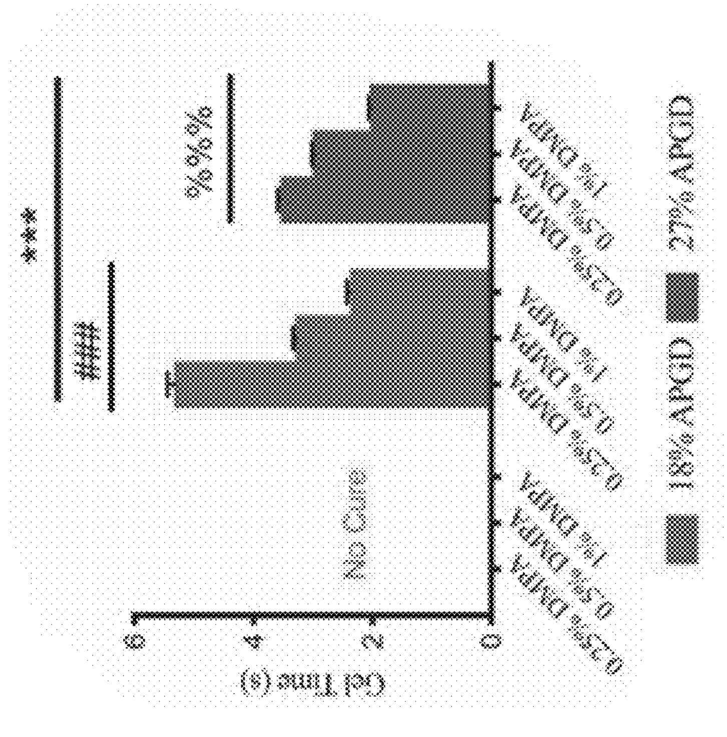

Assessing all APGD resins, increasing acrylation percent can reduce the gel time of the resins regardless of the PI used for crosslinking. Specifically, APGD resin using the DMPA PI did not cure at 9% acrylation, but the resin was able to crosslink at 18 and 27% acrylation (FIG. 10A). The 27% APGD resin can show reduced gel time at all DMPA concentrations compared to the 18% APGD resin ($p<0.0001$). APGD resin with BAPO PI can also exhibit reduced gel times with increasing acrylation percent regardless of PI concentration. Here, the 9% APGD resin can be able to cure at higher concentrations of PI (0.5 and 1% BAPO) and can show significantly higher gel times compared to the 18 and 27% resins (FIG. 10B, $p<0.0001$). The 27% APGD resin can also show lower gel times compared to the 18% resin ($p<0.05$). PI concentration can also affect the gel times of the APGD resins. Increasing DMPA concentration can lead to reduced gel times within both the 18 and 27% APGD resins (FIG. 10A, $p<0.0001$). Increasing BAPO concentration from 0.5 to 1% can reduce gel time of the 9% APGD resin (FIG. 10B, $p<0.0001$), although change in BAPO concentration did not yield effects in the gel time for either the 18 or 27% APGD resins.

Figure 11B:
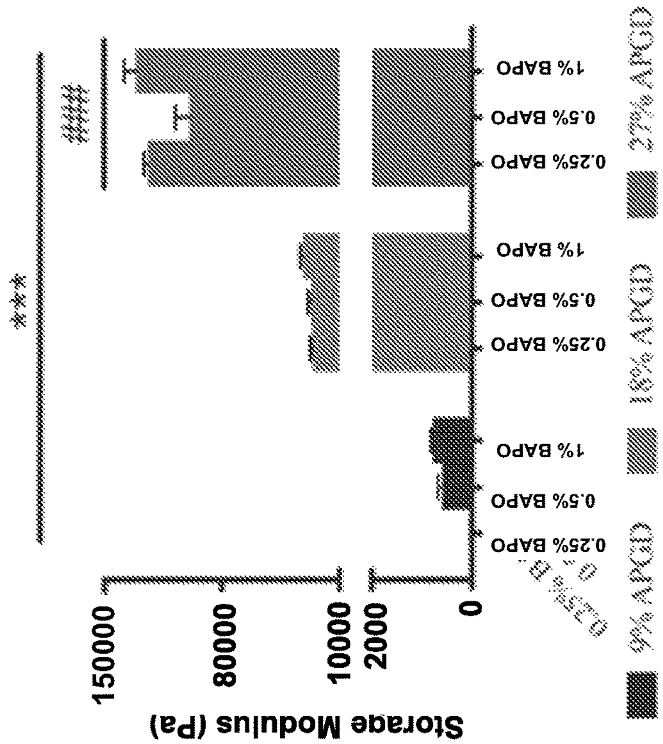
FIGS. 11A and 11B illustrate charts of storage modulus for examples of an implant material in accordance with the present disclosure.
Figure 11A:
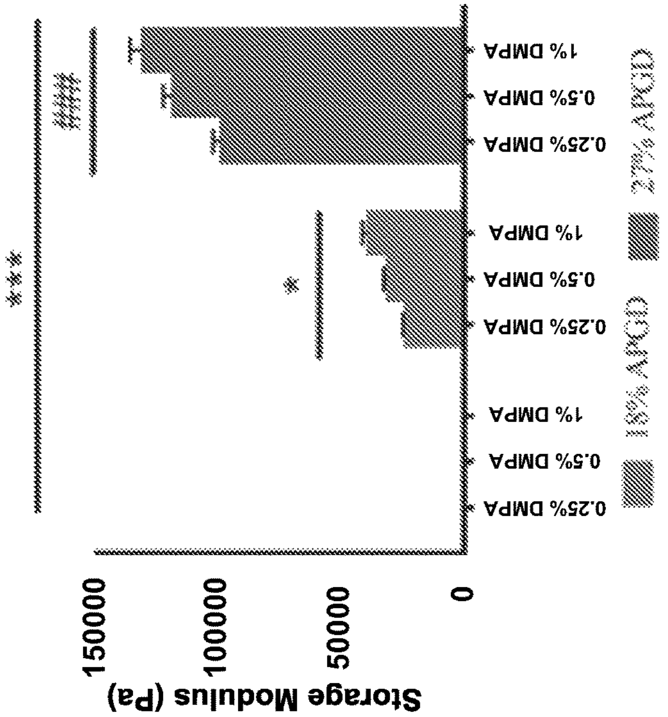

Changes in the storage modulus of the examined APGD resins can mirror the trends noted with the gel times, where increasing acrylation percentage can increase the storage modulus of the APGD resins. Specifically, increasing acrylation percentage can increase APGD resin storage modulus regardless of both the PI used for crosslinking and the PI concentration (FIGS. 11A and 11B, $p<0.0001$). PI concentration can also affect the APGD resin storage moduli. Both 18 and 27% APGD resins with DMPA can show significant increases in storage modulus with increases in PI concentration (FIG. 11A, $p<0.05$ and $p<0.0001$). In the BAPO group, only the 27% APGD resin shows a significant increase in storage modulus due to PI concentration (FIG. 11B, $p<0.0001$).

In addition to analyzing differences due to acrylation percentage and PI concentration, these data can be analyzed to determine whether the use of DMPA versus BAPO as the PI can cause significant differences in resin behavior. There were no significant differences between assessed resin gel times due to PI. The majority of the assessed resin storage moduli showed no differences due to PI. Only the resins with 27% acrylation at 0.25 and 0.5% PI can measure differences due to PI. There were no consistent trends measured in resin complex viscosity, prior to crosslinking, as a function of either acrylation percentage or PI concentration (Table 4). However, these analyses can show the choice of PI affected the viscosity of the resins. Specifically, 18% acrylation resins with DMPA can measure lower complex viscosity versus resins with BAPO at all PI concentrations. At 27% acrylation, resin with DMPA can measure a complex viscosity lower than resin with BAPO at both 0.25 and 1% PI. For the remainder of the present disclosure, 18% APGD with 0.5 wt % PI can be chosen to 3D print samples for testing.

These resins can measure complex viscosity and gel times well below 2 Pa*s and 10 s respectively and did not require high amounts of acrylate crosslinker or PI in order to perform at those benchmarks.

TABLE 4

Material properties of examples of an implant material as a function of acrylation percentage and PI concentration.

Figure 12A:
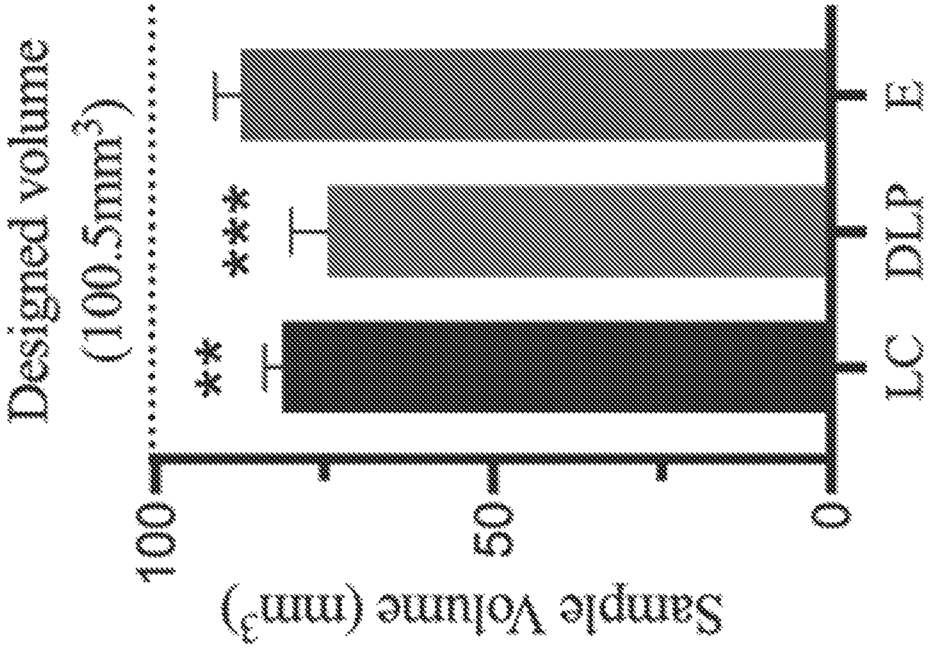
FIGS. 12A and 12B illustrate charts of sample volume and void volume for examples of an implant material in accordance with the present disclosure.
Figure 12B:
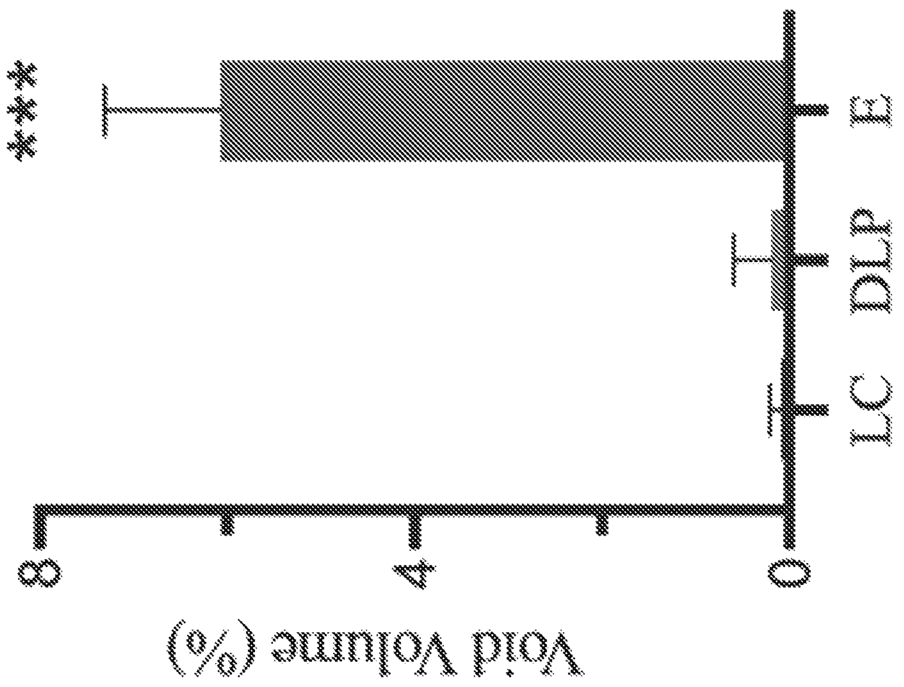

| Resin Formulation | Complex Viscosity Prior to Crosslink (mPa*s) | Gel Time (s) | Storage Modulus at Cure (Pa) |
|---|---|---|---|
| Acrylation %:PI % (DMPA) | | | |
| 9%:0.25% | 0.4 ± 0.03 | N/A | N/A |
| 9%:0.5% | 0.4 ± 0.003 | N/A | N/A |
| 9%:1% | 0.4 ± 0.1 | N/A | N/A |
| 18%:0.25% | 0.4 ± 0.02 | 5.3 ± 0.1 | 24679.6 ± 222.6 |
| 18%:0.5% | 0.5 ± 0.03 | 3.3 ± 0.04 | 32073.9 ± 798.3 |
| 18%:1% | 0.5 ± 0.02 | 2.4 ± 0.1 | 39929.9 ± 1499.7 |
| 27%:0.25% | 0.4 ± 0.04 | 3.6 ± 0.1 | 99897.6 ± 2630.8 |
| 27%:0.5% | 0.4 ± 0.04 | 3.0 ± 0.002 | 119611.3333 ± 3233.0 |
| 27%:1% | 0.4 ± 0.04 | 2.0 ± 0.03 | 131786.3333 ± 4609.4 |
| Acrylation %:PI % (BAPO) | | | |
| 9%:0.25% | 0.7 ± 0.1 | N/A | N/A |
| 9%:0.5% | 0.6 ± 0.01 | 23.3 ± 2.4 | 598.5 ± 87.1 |
| 9%:1% | 0.7 ± 0.03 | 16.5 ± 1.7 | 795.4 ± 34.6 |
| 18%:0.25% | 0.8 ± 01 | 5.5 ± 0.3 | 26522.1 ± 819.6 |
| 18%:0.5% | 0.7 ± 0.04 | 4.1 ± 0.1 | 27562.9 ± 1385.8 |
| 18%:1% | 0.7 ± 0.1 | 2.7 ± 0.2 | 32100.8 ± 1432.9 |
| 27%:0.25% | 0.7 ± 0.03 | 3.4 ± 0.2 | 124383.7 ± 2296.7 |
| 27%:0.5% | 0.5 ± 0.05 | 3.0 ± 0.03 | 99478.6 ± 8238.9 |
| 27%:1% | 0.8 ± 0.08 | 2.2 ± 0.1 | 131466.3 ± 7066.3 |

μCT analysis can be conducted using simple cylinders of 100% infill with representative scan images from each group. Cylinders produced via DLP printing can measure an average volume of 74.6±5.4 $mm^3$ whereas samples produced by LC and E manufacturing can measure volumes of 81.2±2.6 and 87.5±3.7 $mm^3$ respectively. DLP cylinders can be smaller than those produced by both LC and E methods (FIG. 12A, p<0.01 and p<0.0001). LC cylinders can also be smaller than cylinders produced via E printing (p<0.01). All of the sample volumes can be different due to manufacturing modality and all of the samples measured volumes lower than the expected volume for an 8×2 mm cylinder (100.5 $mm^3$). APGD cylinders can also be assessed for void volume as a result of the manufacturing modality (FIG. 12B). Samples produced via LC and DLP methods showed almost no void volume, measuring 0.1±0.1 and 0.2±0.4% void volume, respectively. Conversely, cylinders printed using the E method can measure more void volume compared to LC and DLP samples with 6.1±1.2% void volume (p<0.0001).

Figure 13A:
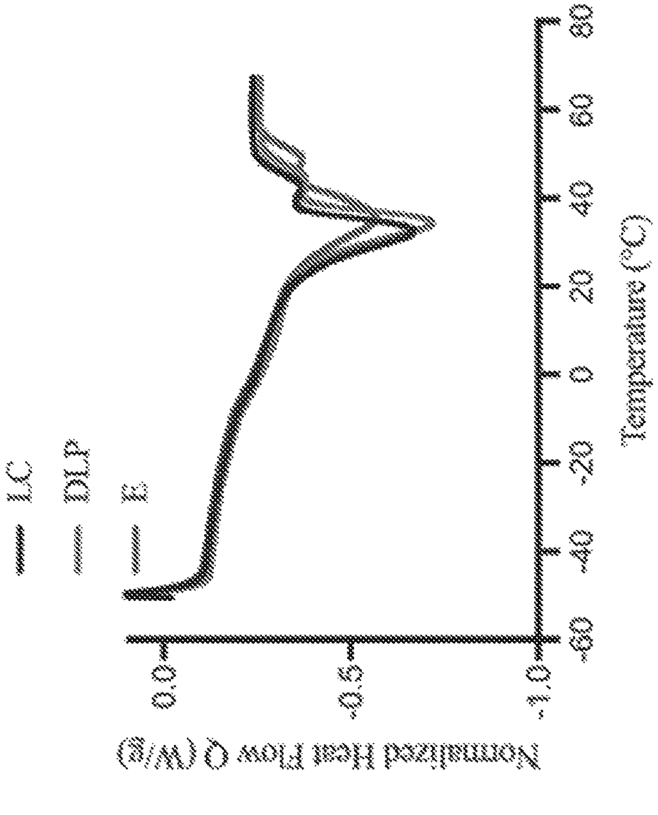
FIGS. 13A and 13B illustrate material properties of an implant material as a function of temperature, in accordance with the present disclosure.
Figure 13B:
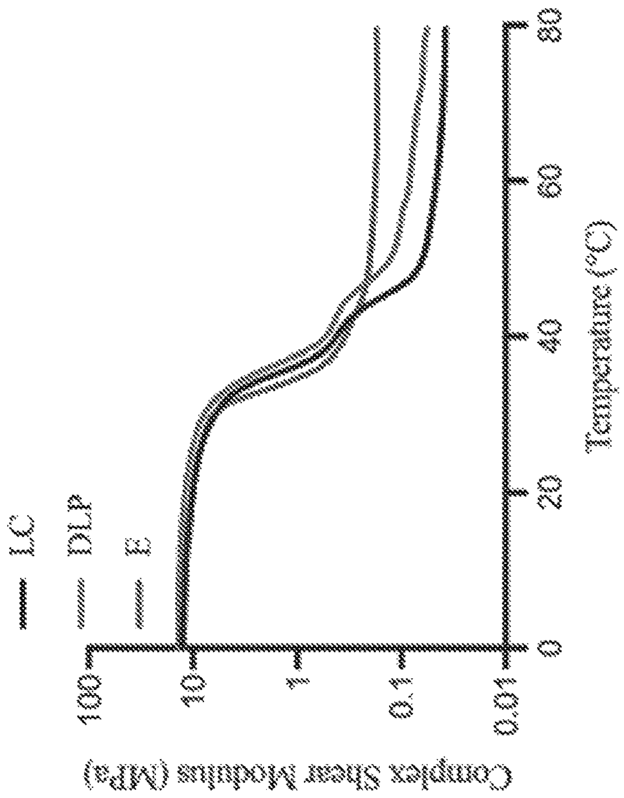

LC and DLP samples can exhibit thermal profiles that appear very similar via DSC (FIG. 13A). However, E samples can show a $T_m$ peak wider than the peaks of LC and DLP samples. Quantitative analysis of DSC data showed no significant differences between sample $T_m$ or $\Delta H_{fusion}$ as a result of manufacturing modality (Table 5). Complex shear modulus can be measured using rheometry over a temperature range that included material behavior below, at, and above APGD transition. Below and at the APGD samples' $T_m$ the complex shear moduli can be similar across manufacturing modalities. However, above the APGD $T_m$, samples can show differences in their rubbery modulus regions. Above $T_m$, E samples can have a larger complex shear modulus compared to DLP samples, which can show a larger complex shear modulus versus LC samples (FIG. 13B). These differences can demonstrate that the manufacturing modality can affect the shear modulus of APGD samples in the rubbery plateau. Rheometry data can also be used to calculate the peak $T_m$ of the APGD samples and as was noted with the DSC data, there were no significant differences in $T_m$ due to manufacturing modality (Table 5).

TABLE 5

$T_m$ measured via DSC and rheometry with enthalpy of fusion.

| | $T_m$ - DSC (° C.) | $\Delta H_{fusion}$ (J/g) | $T_m$ - Rheometry (° C.) |
|---|---|---|---|
| LC | 31.8 ± 1.3 | 46.3 ± 2.2 | 36.4 ± 0.2 |
| DLP | 34.6 ± 0.6 | 50.4 ± 0.4 | 36.6 ± 0.4 |
| E | 35.1 ± 1.7 | 48.8 ± 2.4 | 36.1 ± 0.9 |

Figure 14A:
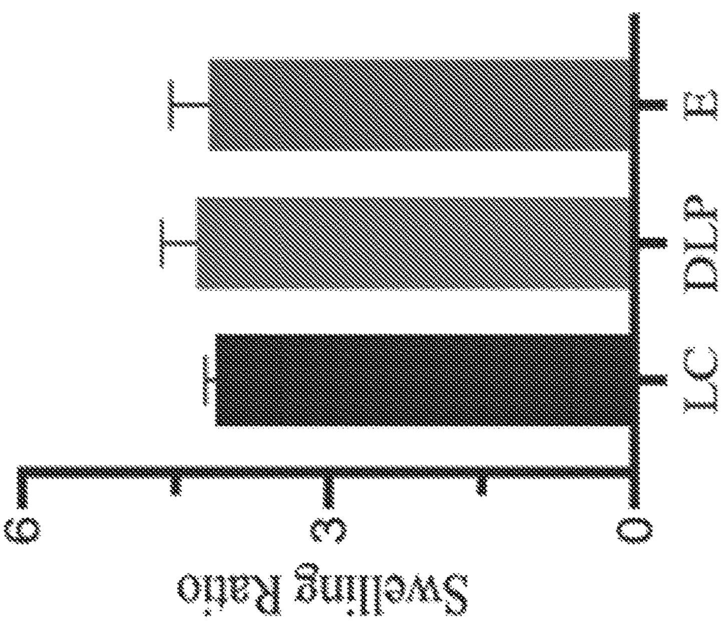
FIGS. 14A and 14B illustrate plots of solvent swelling ratios and gel content, respectively, for examples of an implant material in accordance with the present disclosure.
Figure 14B:
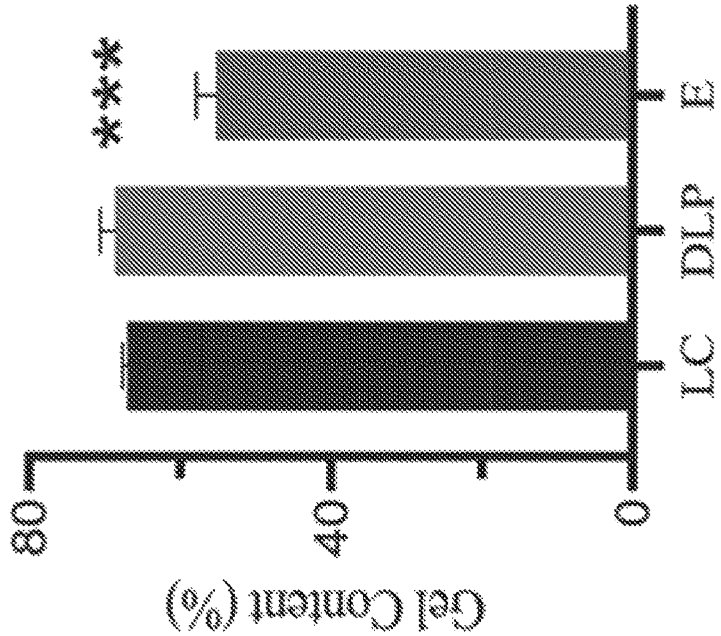

APGD samples can be swollen in THF and swelling ratios of the samples can be recorded. Swelling ratios in THF for the LC, DLP, and E groups were 4.1±0.1, 4.3±0.3, and 4.2±0.4 respectively (FIG. 14A). There were no significant differences between APGD sample swelling ratios due to manufacturing modality. Gel content for E samples can be 55.3±2.6%, while LC and DLP samples can measure 67.0±0.7 and 68.7±1.9% respectively; the gel content of E samples can be lower compared to both the LC and DLP samples (FIG. 14B, p<0.0001).

Figure 15:
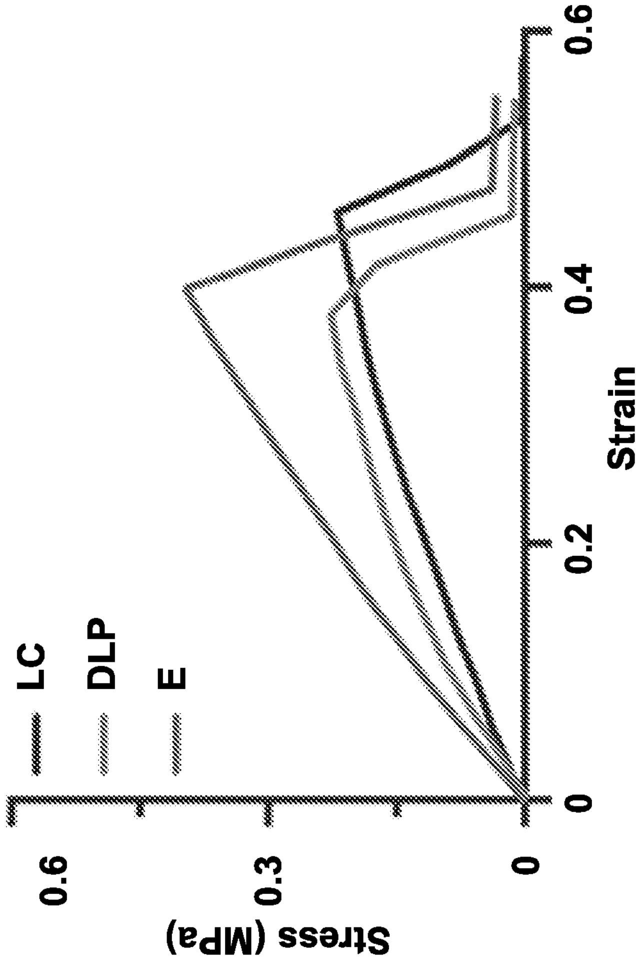
FIG. 15 illustrates a plot of stress-strain curves for examples of an implant material in accordance with the present disclosure.
Figure 16A:
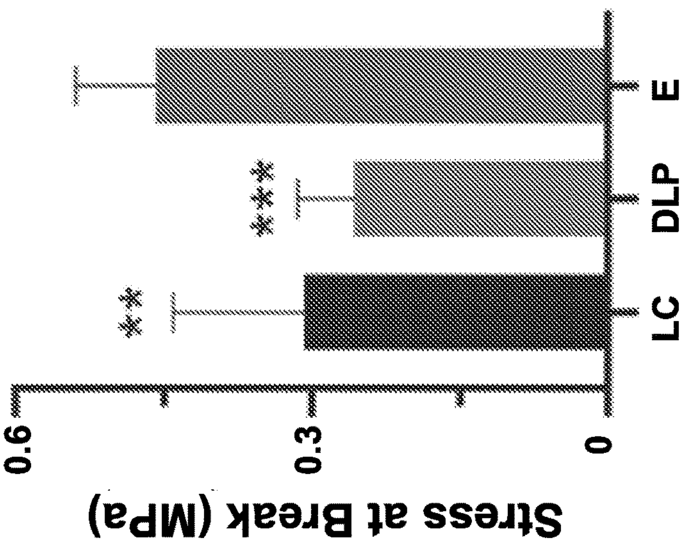
FIGS. 16A and 16B illustrate plots of the stress at break and the strain at break, respectively, for examples of an implant material in accordance with the present disclosure.
Figure 16B:
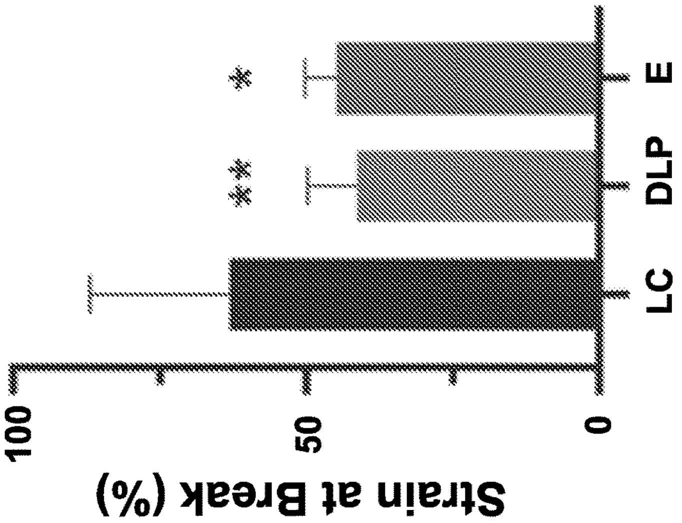

APGD dogbones can be immersed in a water bath set to 37° C. and tested in uniaxial tension until failure. Representative stress-strain data are shown in FIG. 15, where E stress-strain curves can show behavior more similar to linear elastic materials than both LC and DLP samples. Using these experimental data, APGD mechanical behavior can be modelled using the Neo-Hookean non-linear elastic model and the $C_1$ material parameter can be calculated for all samples (Table 6). Both the LC and DLP groups can show lower $C_1$ values compared to the E group (p<. 0001 and p<. 01). All $R^2$ values comparing the experimental versus Neo-Hookean model stress-strain curves can be above 0.95 signifying the accuracy of the Neo-Hookean model fitting. Stress and strain at the point of break can be analyzed for the APGD samples as well. Stress at break for E samples, measured at 0.5±0.1 MPa, can be significantly higher than stress at break compared to both LC and DLP samples, both groups showing stress of 0.3±0.1 MPa (FIG. 16A, $p<0.01$ and $p<.0001$). LC samples can show larger strain at break compared to the 3D printed samples, with a strain at break of 63.2±23.7% (FIG. 16B, $p<0.01$ and $p<0.05$). The DLP and E samples can measure strain at break of 41.5±8.3 and 45.0±5.2% with these two groups not being different. These data can suggest that the 3D printing process itself, regardless of modality, can affect the resultant sample mechanics compared to traditional sample preparation via molding and laser cutting.

TABLE 6

Neo-Hookean model of implant material stress-strain behavior.

| | $C_1$ | $R^2$ |
|---|---|---|
| LC | 0.3 ± 0.1*** | 0.97 ± 0.03 |
| DLP | 0.4 ± 0.2** | 0.97 ± 0.02 |
| E | 0.6 ± 0.1 | 0.995 ± 0.004 |

To measure shape memory behavior of these APGD materials, samples can be set in a programmed shape and can be introduced to 37° C. water to stimulate their shape recovery behavior. $R_f$ quantifies how well the APGD samples maintained their programmed shape, which was being held at room temperature. The LC and DLP groups can both demonstrate high levels of $R_f$, measuring 92.4±6.0 and 97.3±3.7% respectively (Table 7). E samples can show reduced $R_f$ at 77.4±4.7%, which can be lower compared to both the LC and DLP samples ($p<0.0001$). The $R_r$ quantifies how well the APGD samples returned to their permanent shape, after immersion into a 37° C. water bath. All of the APGD samples can demonstrate high levels of $R_r$, with all samples measuring on average above 90% $R_r$ (Table 7). While all of the APGD samples showed high levels of $R_r$, the DLP and E samples can show higher shape recovery compared to LC samples ($p<0.05$ and $p<0.01$ respectively). The speed of the recovery process can also be measured and the 3D printed samples both showed significantly higher $dR_r/dt$ compared to LC samples ($p<0.0001$). Based on these data, manufacturing modality can affect the shape memory behavior of APGD materials throughout the entirety of the shape memory process.

TABLE 7

Shape memory properties of implant materials.

| | LC | DLP | E |
|---|---|---|---|
| $R_f$ (%) | 92.4 ± 6.0 | 97.3 ± 3.7 | 77.4 ± 4.7*** |
| $R_r$ (%) | 93.6 ± 2.1 | 95.8 ± 1.9* | 96.9 ± 1.9** |
| $dR_r/dt$ (rad/min) | 6.6 ± 2.3*** | 12.4 ± 1.1 | 13.6 ± 2.5 |

Prior to 3D printing, a range of resins can be tested in order to determine how acrylation and PI percentage affect the gel time, along with their elastic behavior under shear loading as measured by the sample's storage modulus. The range of 9-27% acrylation can be chosen. Samples can be tested with 18-36% acrylation and all of them cured without issue. Given the interest for clinical translation of APGD, and the desire to limit the amount of acrylate monomers to due to potential adverse effects on cells, it can be important to determine the acrylation percent at which APGD resin curing can begin to exhibit failure of crosslinking. 9% acrylation can be shown to be an appropriate lower bound for APGD resin, as this acrylation percentage led to inconsistent curing. 27% APGD can be chosen as the upper bound of acrylation percentage because 36% APGD exhibited a $T_m$ lower than room temperature, rendering its shape memory capabilities less viable for clinical applications.

Table 8 provides a summary of the effects of APGD chemistry on resin photorheometrical behavior. Overall, both acrylation and PI percentage can affect APGD resin gel time and storage modulus, however acrylation percentage can be the more influential parameter (see, e.g., FIGS. 10A, 10B, 11A, 11B). Regardless of the PI or PI concentration, increasing acrylation percentage can cause significant reductions in APGD resin gel time and significant increases in cured APGD storage modulus. Increasing acrylation percentage can increase the number of acrylate side chains on the PGD backbone available for crosslinking, which can reduce the time to reach the gel point as more crosslinking occurs. Conversely as the APGD resins transition from a liquid to a solid during the curing process, it follows that those with a higher crosslink density can exhibit larger storage moduli as they are able to store more energy being imparted into the polymer network. PI concentration can also affect APGD resin gel time and storage moduli. For 18 and 27% APGD with DMPA, increasing DMPA concentration can reduce gel times and increase storage moduli across all PI concentrations. Interestingly, the 9% APGD resin was unable to cure regardless of DMPA concentration, but it can be able to cure using BAPO as the PI at 0.5 and 1 wt %. Despite being able to cure, the 9% APGD resins with BAPO can show gel times in the range of 15-25 s which can be higher than all other groups that cured, suggesting the use of these resins for DLP 3DP would not produce good device prints due to long layer exposure times. 18% APGD resin using BAPO can also show a significant reduction in gel time with increasing BAPO concentration. The storage moduli of these samples can appear less impacted by PI concentration compared to the samples using DMPA. Without wishing to be bound by any particular scientific theory, this may be due to differences in chemistry between DMPA and BAPO, with BAPO being more effective at catalyzing this acrylate crosslinking reaction compared to DMPA.

TABLE 8

Effect summary of tested variables on shape memory resin material properties

| | Acrylation % (↑) | PI % (↑) | PI |
|---|---|---|---|
| Gel Time | ↓ | ↓ | — |
| Storage Modulus | ↑ | ↑ | — |
| Complex Viscosity | — | — | ↑ (BAPO) |

The use of DMPA and BAPO as PIs can be directly compared across the APGD resins for 18 and 27% acrylation and for all PI concentrations. The major difference in APGD resin behavior due to PI used can be that nearly all APGD resins using BAPO can measure higher complex viscosities prior to crosslinking compared to APGD resins synthesized with DMPA. Without wishing to be bound by any particular scientific theory, this can simply be due to the necessity to add a photoabsorbent to APGD resin with BAPO, but not those with DMPA, as a result of the requirements of DLP 3D printing. Importantly, even considering the increase in complex viscosity, none of the APGD resins measured complex viscosities close to the 2 Pa*s upper limit established in this work for effective 3D printing. APGD resin gel times and storage moduli showed no significant differences due to PI for the majority of groups assessed. Based on these data, APGD resin with 18% acrylation and 0.5 wt % PI can be chosen. These resins can measure well within the complex viscosity and gel time restrictions of 2 Pa*s and 10 s respectively. The use of the intermediate acrylation percent and PI concentration can also provide a good balance between the benefits of higher crosslink percentage, more reliable curing and faster gel times, and the desire to avoid high levels of acrylate within these resins. This particular APGD resin can also be shown to have potential for cell attachment and proliferation.

The present disclosure can characterize the physicochemical, mechanical, and shape memory behavior of 3D printed APGD and can determine how the two 3D printing modalities affected sample material properties (Table 9). Although 3D printing can produce complex geometries using a resin, like all manufacturing modalities it can produce discrepancies from the intended design. For this reason, the volumes of APGD samples can be measured to provide a better understanding of the accuracy of the different manufacturing modalities used throughout this work. The samples scanned via μCT can be 2×8 mm cylinders with a designed volume of approximately 100.5 $mm^3$. All of the scanned APGD samples can measure volumes below this expected volume, where DLP samples can have volumes lower than both LC and E samples and LC samples can have volumes significantly lower than E samples.

The LC and DLP sample volumes can be lower than anticipated likely due to the thickness of the samples, without wishing to be bound by any particular scientific theory. While the LC process itself is very accurate, cutting samples from APGD sheets with precise diameters, the thickness of the sample is not always consistent as it is dependent on the exact volume of APGD set into the mold prior to cutting. This volume is not always exactly the same and as such this causes slight differences in the thickness of the samples. The DLP samples can be very similar in that the dimensions of printed objects can be highly accurate in the X and Y planes, but in the Z direction the printer can be routinely biased towards producing samples thinner than anticipated when compared to the submitted STL file. This accuracy issue could be due to multiple factors including errors with the conversion of computer aided design (CAD) files to STL files, non-optimized 3D printer setup parameters, or material post-cure shrinkage. However, these accuracy issues are minor and, unlike the volume discrepancies noted for the LC process, this issue of thinner prints is easily rectified by increasing the thickness of the STL.

TABLE 9

Effect summary of manufacture modality on implant materials.

| | LC | DLP | E |
|---|---|---|---|
| Sample Volume | ↑(DLP), ↓(E) | ↓(LC, E) | ↑(LC, DLP) |
| Void Volume | ↓(E) | ↓(E) | ↑(LC, DLP) |
| $T_m$ | — | — | — |
| $\Delta H_{fusion}$ | — | — | — |
| Complex Shear Modulus | ↓(DLP, E) | ↑(LC), ↓(E) | ↑(LC, DLP) |
| Swelling Ratio | — | — | — |
| Gel Content | ↑(E) | ↑(E) | ↓(LC, DLP) |
| $C_1$ | ↓((E) | ↓(E) | ↑(LC, DLP) |
| Stress at Break | ↓((E) | ↓(E) | ↓(LC, DLP) |
| Strain at Break | ↑(DLP, E) | ↓(LC) | ↓(LC) |
| $R_f$ | ↑(E) | ↑(E) | ↓(LC, DLP) |
| $R_r$ | ↓(DLP, E) | ↑(LC) | ↑(LC) |
| $dR_r/dt$ | ↓(DLP, E) | ↑(LC) | ↑(LC) |

The reduced volume of E samples was not due entirely due to mismatches in STL versus print geometries. Instead, the E process can introduce a higher level of void volume in the APGD samples as compared to samples prepared via LC and DLP methods. This increased void volume can likely be what led to the E samples exhibiting lower than expected volumes when measured via μCT. The void volume differences across the APGD samples can be directly related to the manufacturing process of the different modalities used. In the preparation of the LC and DLP samples, the APGD resin can be fully melted to either pipette APGD into a mold or onto the print bed of the DLP printer. As such, the void volume can be introduced via micro bubbles that are trapped in the melted APGD resin. With careful preparation these bubbles can largely be removed from the resin and in turn the resultant samples can yield very low void volume. The E printing process for APGD can be very different in that the resin cannot be completely melted as the resin melt lacks the viscosity to retain the proper filament stability prior to photocuring. The APGD resin can be heated in the print head until it is malleable enough to be extruded via the attached air compressor, but it is possible that gaps existed in the resin prior to extrusion which were not removed by melting, or which form between filament layers throughout the printing process causing increased void volume. Potential ways to reduce this issue can include increasing the viscosity of the APGD resin via increasing its molecular weight or potentially using Freeform Reversible Embedding of Suspended Hydrogels (FRESH) 3D printing such that fully melted resin will always be supported by surrounding sacrificial material.

Based on the Mather classification of shape memory polymers, APGD can be a chemically crosslinked semi-crystalline rubber that undergoes a melt transition when exposed to temperatures at or above its $T_m$. DSC and rheometry analysis can increase acrylation percentage, which can induce increased polymer network crosslink density, can be shown to reduce APGD $T_m$ and $\Delta H_{fusion}$. The present disclosure can determine whether differences in manufacturing modality can affect APGD $T_m$ or relative crystallinity as measured by $\Delta H_{fusion}$. Assessing the DSC data, there were no significant differences between either $T_m$ or $\Delta H_{fusion}$ due to manufacturing modality (Table 5). $T_m$ as measured by rheometry also showed no significant differences as a function of manufacturing modality.

Although the use of different PIs did not influence $T_m$ or $\Delta H_{fusion}$ across any manufacturing modality, the complex shear moduli in the rubbery modulus region can be clearly affected (FIG. 13B). Specifically, the E samples can exhibit the stiffest response under shear loading followed by the DLP and LC samples respectively. The E samples exhibiting the stiffest response in shear can be due to the default settings of the E printer, which can print with a rectilinear 0/90° raster orientation. This pattern of printing can increase the stiffness of tested samples in tensile testing, although there is little consideration of these effects under shear loading to date. While DLP printing has no raster orientation to influence print mechanics, it can cure the APGD resin via individual discrete layers into the final object as programmed by the submitted STL file. This could lead to crosslink organization throughout the structure sequestered largely within individual layers with minimal interaction between layers other than directly at points of curing. When curing LC samples, the entirety of the APGD resin volume can be exposed to UV light simultaneously, allowing for crosslinking to occur randomly throughout the bulk of the sample. As such, crosslinks in LC samples will not be organized via discrete layers, like those in the DLP samples, but instead can be randomly oriented throughout the volume of the LC sample. Through computational modeling, differences in polymer crosslink orientation can play a significant role in the mechanics of polymer networks. Specifically, modeling the stress-strain behavior of polymer networks with either random or organized crosslink orientations can show that polymer networks with randomly aligned crosslinks can yield less stiff behavior compared to those materials with organized crosslinks. For these reasons, potential differences in crosslink orientation can be part of the underlying cause for the differences measured in APGD sample shear moduli due to manufacturing modality.

Swelling assays using organic solvents can be a typical means of determining the crosslink density and the relative crosslink percentage of thermal or photocured elastomers. The relationship between swelling ratio and crosslink density can be inversely proportional, while the relationship between gel content and relative crosslink percentage can be directly proportional. Increasing acrylation percentage can be shown to decrease APGD swelling ratio and increase APGD gel content. Here, tested APGD resins can have uniform acrylation and PI percentage allowing for the determination of whether the different manufacturing modalities contributed to differences in APGD crosslinking.

FIGS. 14A and 14B shows the swelling ratios and gel contents of the APGD samples manufactured via LC, DLP, and LC methods. There were no significant differences between sample swelling ratios, however the gel content of the E samples can be lower than the gel contents of the LC and DLP groups ($p<0.0001$). The swelling ratio can provide information on how much solvent the samples are able to absorb, while the gel content can take into account the mass of the samples after the solvent has been removed. More crosslinks present in an elastomer sample can lead to less chain mobility when exposed to a solvent, causing less unreacted monomer (sol content) to be removed from the sample by the solvent, which can result in a larger gel content measurement. As such, the E samples measuring a lower gel content compared to the LC and DLP samples can suggest that the E 3D printing method disclosed herein can produce APGD samples with lower relative crosslink percentage compared to the LC and DLP methods.

Given the lower gel content of the E samples, the expectation can be that the E samples can measure a significantly higher swelling ratio as well, but this was not the case. An integral part of the calculation for a sample's swelling ratio, and its subsequent crosslink density, can be the consideration of the sample's density. Given that the E samples were shown to have significantly higher void volume compared to the LC and DLP samples, the density of the E samples can be different compared to the LC and DLP groups providing a confounding variable that led to these groups not measuring significantly different swelling ratios (FIG. 12A). Specifically, additional void volume in E samples can cause less solvent to be absorbed compared to the scenario where those voids were filled with APGD causing a reduction in the maximum possible swelling ratio. Conversely, the gel content can remain unaffected by the void volume as gel content is not dependent on sample density, but on the mass of the samples prior to and after swelling. Therefore, the results of the gel content measurement can be more instructive regarding how the E 3D printing process affects the crosslinking of APGD samples.

The E samples measuring a lower relative crosslink percentage can be expected for multiple reasons. When assessing the DSC thermograms of all the APGD samples, the E samples can yield wider and more heterogeneous transition peaks compared to the LC and DLP samples (FIG. 13A). While these differences in the DSC thermograms are qualitative, the same trends can be measured where increasing APGD crosslink density can lead to tighter more homogenous transition peaks. This reduction in E sample crosslink percentage can also play a role in the increased stiffness seen in the rubbery plateau region of the E rheometry samples (FIG. 13B).

Understanding the behavior of APGD at 37° C. can be used for its translation to clinical applications, which is why both the tensile testing and shape memory assays can be performed in water at body temperature. Assessing the tensile mechanics of the APGD specimens, the C1 parameters for the LC and DLP groups can be lower compared to the E group (Table 6). This can indicate that the E samples measured stiffer behavior compared to the other groups, as assessed by Neo-Hookean nonlinear elastic fitting. In addition, the stress at break of the E samples can be larger than that of both the LC and DLP samples (FIG. 16A). Conversely, the strain at break of the LC samples can be larger than the strain at break for both 3D printed groups (FIGS. 15, $p<0.01$ and $p<0.05$ for DLP and E groups respectively). Without wishing to be bound by any particular scientific theory, it does appear that the E samples can demonstrate the stiffest tangent linear behavior of the 3 tested groups. Conversely, LC samples can be more elastic, and perhaps less stiff, than the samples printed either using the DLP or E methods. This result can align with what was measured during the rheometry tests, where the LC samples showed lower rubbery moduli compared to the DLP and E samples. This further suggests that the likely random orientation of the LC sample crosslinks can lead to less stiff samples compared to the ordered orientation of the crosslinks likely created by the DLP and E methods. Overall, the DLP samples measured both the lowest stress and strain at break, but it is possible that the mechanics of these samples can be adjusted through post-processing methods.

The shape memory data for all APGD samples can be comparable or better than previous shape memory behavior of APGD samples, other than the low $R_f$ recorded for E samples which can be lower than $R_f$ measurements from LC and DLP samples (Table 7, $p<0.0001$). This reduced $R_f$ can be due to the increased void volume and subsequent loss of crystalline regions important for fixing the temporary shape of the sample compared to the LC and DLP samples. All APGD samples can show $R_r$ over 90%, however the 3D printed groups both showed increased $R_r$ compared to the LC samples ($p<0.05$ and $p<0.01$ for DLP and E respectively). The 3D printed samples can also show significantly faster $R_r$ versus the LC samples ($p<0.0001$). Given that crosslink orientation can be playing a role in the mechanics of manufactured APGD specimens, it can be possible that crosslink orientation affects these samples' shape memory behavior. Without wishing to be bound by any particular scientific theory, it can follow that samples 3D printed directly into the desired permanent shape can yield improved shape memory capabilities compared to APGD set in a mold and laser cut to provide individual specimens. When 3D printed samples are cured into their permanent shape, crosslinks can organize in the geometry of that shape due to the layering of the 3D printing process itself, whereas when APGD is in a mold, crosslinking can take place through the entirety of the volume at the same time and presumably in an entirely random pattern. Samples with crosslinks ordered towards the geometry of the permanent shape can show improved and faster recovery compared to samples with randomly oriented crosslinks.

The final test of the utilized manufacturing modalities can be whether they could be used to produce complex geometries. Only the DLP method was capable of producing high quality prints of complex anatomical structures. Making models of an ear or nose would not be possible with APGD in a mold, due to the constraints of lighting and the ability to recover the material from the mold undamaged after the curing process has taken place. E printing can be capable of producing the ear sample although at much lower quality compared to the DLP counterpart. Part of the loss in quality can be due to the erroneous extrusion of resin during routine movement of the printhead between layers of the print. While it can be possible to remove this excess extrusion via manual modification of printer geometric code (G-code). While the E printer can be capable of producing the ear sample, it was unable to produce a nose sample due to lack of quality support material that works in tandem with APGD. It can be possible to print complex structures using APGD with a higher quality E printer setup, or potentially using other types of E printing technology such as FRESH or inkjet 3D printing. Ultimately the DLP printer can provide excellent samples that were accurate to the programmed STL file and maintained excellent shape memory behavior.

As disclosed herein, a range of APGD resin cure kinetics can be characterized, DLP printing of APGD can be established, and significant differences in APGD sample behavior due to their underlying method of manufacture can be demonstrated. The characterization of APGD resin cure kinetics can highlight that for this polymer system the dominant factor in adjusting the APGD gel time can be the acrylation percentage as opposed to the PI concentration. The stiffness in shear loading of the resultant cured APGD can also be largely dependent on the crosslink density as opposed to the PI percentage as well. Overall, the PI used did not significantly affect resin gel time or storage modulus, but it can affect resin viscosity. Additionally, these data can provide preliminary print parameters for the DLP, and E systems used herein. With high throughput, excellent resolution, and the capability to produce complex anatomical structures demonstrating shape memory capabilities, this result can be highly translationally relevant.

Additionally, the number of 3D printable resins that exhibit shape memory and biodegradable properties can be very limited, placing DLP 3D printable APGD in an excellent position to explore the production of novel devices for minimally invasive clinical applications. Manufacturing modality can play a major role in APGD sample behavior, where some of the differences can fall along the lines of 3D printed versus molded samples. Notably, the molded samples can be able to undergo more strain than the 3D printed samples during tensile tests but measured lower shape recovery compared to the 3D printed samples. Differences can also arise between the 3D printed groups as well, where E samples can be stiffer in both shear and tensile loading than DLP samples. E samples can measure higher levels of void volume and lower levels of crosslinking versus both the LC and DLP groups. Understanding the differences in the APGD samples engendered by different manufacturing modalities can be used for future use of APDG relying on an application specific manufacture modality.

While the present disclosure has been described in connection with a plurality of exemplary aspects, as illustrated in the various figures and discussed above, it is understood that other similar aspects can be used, or modifications and additions can be made to the described aspects for performing the same function of the present disclosure without deviating therefrom. For example, in various aspects of the disclosure, methods and compositions were described according to aspects of the presently disclosed subject matter. However, other equivalent methods or composition to these described aspects are also contemplated by the teachings herein. Therefore, the present disclosure should not be limited to any single aspect, but rather construed in breadth and scope in accordance with the appended claims.

What is claimed is:

1. A material comprising:

a shape memory polymer having a first shape and a second shape, the shape memory polymer comprising:

a polymer backbone having at least one monomer unit of glycerol and at least one monomer unit of dodecanedioate;

a photocurable side chain bonded to the polymer backbone; and a photoinitiator.

2. The material of claim 1, wherein:

the shape memory polymer is programmed in the first shape by a first stimulus; and the shape memory polymer is in the first shape and takes the second shape in response to a second stimulus.

3. The material of claim 2, wherein the first stimulus comprises visible light, ultraviolet light, infrared light, or a combination thereof.

4. The material of claim 2, wherein the photocurable side chain comprises one or more of: acrylate, methacrylate, thiolene, norbornene, and/or cinnamate.

5. The material of claim 2, wherein the photoinitiator comprises one or more of: 2,2-Dimethoxy-2-phenylacetophenone (DMPA), Phenylbis(2,4,6-trimethylbenzoyl)phosphine oxide (BAPO), monoacylphosphine oxide (MAPO), 2,2'-azobis[2-methyl-N-(2-hydroxyethyl) promionamide] (VA-086), and/or riboflavin.

6. The material of claim 2, wherein the shape memory polymer has a melt transition temperature from approximately 25° C. to approximately 45° C.

7. The material of claim 6, wherein the shape memory polymer is an elastomer above the melt transition temperature and a thermoplastic below the melt transition temperature.

8. The material of claim 2, wherein the shape memory polymer comprises pores ranging from about 0.05 mm to about 10 mm.

9. The material of claim 2, wherein the second shape is a compressed shape for minimally invasive delivery.

10. The material of claim 2, wherein the shape memory polymer further comprises a functionalized surface.

11. The material of claim 1, wherein:

the material is an implant material;

the shape memory polymer further comprises a functionalized surface;

the photocurable side chain comprises one or more of: acrylate, methacrylate, thiolene, norbornene, and/or cinnamate;

the photoinitiator comprises one or more of: 2,2-Dimethoxy-2-phenylacetophenone (DMPA), Phenylbis(2,4,6-trimethylbenzoyl)phosphine oxide (BAPO), monoacylphosphine oxide (MAPO), 2,2'-azobis[2-methyl-N-(2-hydroxyethyl) promionamide] (VA-086), and/or riboflavin;

the shape memory polymer is programmed in the first shape by a first stimulus;

the shape memory polymer is in the first shape and takes the second shape in response to a second stimulus;

the shape memory polymer has a melt transition temperature from approximately 25° C. to approximately 45° C.; and the shape memory polymer comprises pores ranging from about 0.05 mm to about 10 mm.

12. The material of claim 11, wherein the functionalized surface comprises at least one functional group.

13. The material of claim 12, wherein at least one functional group comprises a bioactive agent.

14. The material of claim 11, wherein the molar ratio of the at least one monomer unit of glycerol to the at least one monomer unit of dodecanedioate is from approximately 10:1 to approximately 1:10.

15. The material of claim 11, wherein the implant material has a biodegradation time when implanted in vivo from approximately 4 months to approximately 24 months.

16. A method of making the material of claim 1 in a form selected from the group consisting of an implant, a patterned mesh, and a molded medical device comprising:

forming a shape memory resin comprising the polymer backbone;

acrylating the shape memory resin to have the photocurable side chain;

adding the photoinitiator to the shape memory resin; and curing the shape memory resin to form the material.

17. The method of claim 16 further comprising:

printing the shape memory resin by additive manufacturing;

wherein:

the curing comprises exposing the shape memory resin to visible, UV, or infrared light;

the form of the material is an implant material selected from the group consisting of a sheet, a membrane, a mesh, a sponge, a patch, a molded medical device, and a combination thereof; and the implant material is in the first shape and takes the second shape in response to a stimulus.

18. The method of claim 17, wherein the shape memory resin is printed with organic or inorganic constituents of tissue extracellular matrices comprising one or more of: hydroxyapatite, calcium phosphate, carbonated apatite, and decellularized and/or lyophilized soft tissues.

19. The method of claim 17 further comprising:

post-thermally curing the implant material to form ester crosslinks and photosensitive molecular crosslinks.

20. The method of claim 19, wherein the post-thermally curing is varied to control a number of crosslinks.

21. The method of claim 17 further comprising:

heating the implant material;

wherein the implant material is in the first shape and takes the second shape in response to the heating.

22. The method of claim 17, wherein the implant material has a melt transition temperature from approximately 25° C. to approximately 45° C.

23. The method of claim 17, wherein the implant material is an elastomer in the first shape and a thermoplastic in the second shape.

24. The method of claim 17 further comprising:

functionalizing a surface of the implant material;

wherein the functionalized surface comprises a bioactive agent.

* * * * *